US010302723B2

(12) United States Patent
Manikis et al.

(10) Patent No.: US 10,302,723 B2
(45) Date of Patent: May 28, 2019

(54) APPARATUSES, METHODS AND SYSTEMS FOR ESTIMATING WATER DIFFUSIVITY AND MICROCIRCULATION OF BLOOD USING DW-MRI DATA

(71) Applicant: Foundation for Research and Technology - Hellas (FORTH), Heraklion, Crete (GR)

(72) Inventors: Georgios Manikis, Crete (GR); Eleftherios Kontopodis, Crete (GR); Konstantinos Marias, Crete (GR)

(73) Assignee: FOUNDATION FOR RESEARCH AND TECHNOLOGY —HELLAS (FORTH), Heraklion (GR)

( * ) Notice: Subject to any disclaimer, the term of this patent is extended or adjusted under 35 U.S.C. 154(b) by 545 days.

(21) Appl. No.: 14/940,745

(22) Filed: Nov. 13, 2015

(65) Prior Publication Data
US 2016/0139226 A1 May 19, 2016

Related U.S. Application Data

(60) Provisional application No. 62/080,126, filed on Nov. 14, 2014.

(51) Int. Cl.
| | |
|---|---|
| *G06F 7/60* | (2006.01) |
| *G06F 17/10* | (2006.01) |
| *G01R 33/56* | (2006.01) |
| *G16H 50/50* | (2018.01) |
| *G01R 33/563* | (2006.01) |
| *A61B 5/055* | (2006.01) |

(52) U.S. Cl.
CPC ..... *G01R 33/5608* (2013.01); *G01R 33/56341* (2013.01); *G06F 17/10* (2013.01); *G16H 50/50* (2018.01); *A61B 5/055* (2013.01)

(58) Field of Classification Search
CPC .................................................. G01R 33/5608
USPC .......................................................... 703/2
See application file for complete search history.

(56) References Cited

PUBLICATIONS

Bihan Le D. et al., "Separation of Diffusion and Perfusion in Intravoxel Incoherent Motion MR Imaging," Radiology, Radiological Society of North America, Inc., US, vol. 168, No. 2, Jan. 1, 1988, pp. 497-505.

(Continued)

*Primary Examiner* — Timothy A Mudrick
(74) *Attorney, Agent, or Firm* — Norton Rose Fulbright US LLP

(57) ABSTRACT

("AEW") are disclosed herein. The apparatuses, methods and systems provide a computational framework for choosing and applying the most appropriate model in different regions of a heterogeneous area on a voxel-by-voxel basis. The apparatuses, methods and systems also configure an intravoxel-incoherent-motion (IVIM) model for estimating water diffusivity and microcirculation of blood in the capillary network from DW-MRI low b-value data. In one implementation, the method uses a small number of b-values (at least 3 in the b-value range of 0-300 s/mm², increasing the upper bound of the low b-value range by one b-value in the absence of DW-MRI signal at 300 s/mm² and is able to synthetically generate DW-MRI data corresponding at higher b-values using the derived IVIM equation. The method also accounts for estimating non-Gaussian diffusion parameter $K_{app}$.

12 Claims, 23 Drawing Sheets

An exemplary flowchart of the Reduced b-values Incoherent Motion (REbIM) model

(56) References Cited

PUBLICATIONS

Dow-Mu Koh et al.: "Intravoxel Incoherent Motion in Body Diffusion-Weighted MRI: Reality and Challenges", *American Journal of Roentgenology*, vol. 196, No. 6, Jun. 1, 2011, pp. 1351-1361.

Padhani A. R. et al., "Diffusion-Weighted Magnetic Resonance Imaging as a Cancer Biomarker: Consensus and Recommendations," *Neoplasia*, Neoplasia Press, Ann Arbor, MI, US, vol. 11, No. 2, Feb. 1, 2009, pp. 102-125.

E. E. Sigmund et al., "Intravoxel Incoherent Motion Imaging of Tumor Microenvironment in Locally Advanced Breast Cancer", *Magnetic Resonance in Medicine*, vol. 65, No. 5, Feb. 1, 2011, pp. 1437-1447.

Hildebrand Dijkstra et al., "Effects of microperfusion in hepatic diffusion weighted imaging", *European Radiology*, Springer, Berlin, DE, vol. 22, No. 4, Nov. 12, 2011, pp. 891-899.

Belmonte G. et al., "Sensitivity and specificity of prostate tumor discrimination by IVIM approximation", *Proceeding of the International Society for Magnetic Resonance in Medicine*, 22nd Annual Meeting and Exhibition, Milan, Italy, May 10-16, 2014, vol. 22, Apr. 25, 2014, p. 4541.

Freiman, Moti et al., "In Vivo assessment of optimal b-value range for perfusion-insensitive apparent diffusion coefficient imaging", *Medical Physics, AIP*. Melville, NY, US, vol. 39, No. 8, Jul. 20, 2012, pp. 4832-4839.

Freiman, Moti et al., "Reliable estimation of incoherent motion parametric maps from diffusion-weighted MRI using fusion bootstrap moves," *Medical Image Analysis*, vol. 17, 2013, pp. 325-336.

Taimouri, V et al., "Spatially constrained incoherent motion method improves diffusion-weighted MRI signal decay analysis in the liver and spleen," *Medical Physics*, vol. 42, No. 4, Apr. 2015, pp. 1895-1903.

Ogura, A. et al, "Evaluation of intravoxel incoherent motion using the Fourier analysis for prostate cancer," *European Society of Radiology*, 2015, pp. 1-14.

Voert, E. et al., "Intravoxel Incoherent Motion Protocol Evaluation and Data Quality in Normal and Malignant Liver Tissue and Comparison to the Literature," *Investigative Radiology*, vol. 51, No. 2, Feb. 2016, pp. 90-99.

International Search Report and Written Opinion, dated May 23, 2016 for PCT International Application No. PCT/EP2015/076678, filed Nov. 16, 2015.

Lemke, A. et al., "Toward an optimal distribution of b values for intravoxel incoherent motion imaging,"Magnetic Resonance Imaging, vol. 29, No. 6, pp. 766-776, 2011, doi: 10.1016/j.mri.2011.03.004.

Penner, A.H. et al., "Intravoxel incoherent motion model-based liver lesion characterisation from three b-value diffusion-weighted MRI,"European Radiology, vol. 23, No. 10, pp. 2773-2783, 2013, doi: 10.1007/s00330-013-2869-z.

Liu, C. et al., "Intravoxel incoherent motion (IVIM) in evaluation of breast lesions: comparison with conventional DWI,"European Journal of Radiology, vol. 82, no. 12, pp. e782-9, 2013, doi:10.1016/j.ejrad.2013.08.006.

Alberich-Bayarri, A. et al., "Optimisation of b-values in MR diffusion-weighted acquisitions through information theory: a mathematical justification for consensus,"ECR 2014-24th European Congress of Radiology, Mar. 6-10, 2014, Vienna, Austria. doi: 10.1594/ecr2014/B-0580.

Cho, G.Y. et al., "Comparison of fitting methods and b-value sampling strategies for intravoxel incoherent motion in breast cancer,"Magnetic Resonance Medicine, vol. 74, No. 4, pp. 1077-1085, 2015, doi: 10.1002/mrm.25484.

Zhang, J.L. et al., "Optimization of b-value sampling for diffusion-weighted imaging of the kidney,"Magnetic Resonance Medicine, vol. 67, No. 1, pp. 89-97, 2012, doi: 10.1002/mrm.22982.

Dyvorne, H. et al., "Intravoxel incoherent motion diffusion imaging of the liver: optimal b-value subsampling and impact on parameter precision and reproducibility,"European Journal of Radiology, vol. 83, No. 12, pp. 2109-2113, 2014, doi: 10.1016/j.ejrad.2014.09.003.

Jambor, I. et al., "Optimization of b-value distribution for biexponential diffusion-weighted MR imaging of normal prostate,"Journal of Magnetic Resonance Imaging, vol. 4, No. 5, pp. 1213-1222, 2014, doi: 10.1002/jmri.24271.

Döpfert, J. et al., "Investigation of prostate cancer using diffusion-weighted intravoxel incoherent motion imaging,"Magnetic Resonance Imaging, vol. 29, No. 8, pp. 1053-1058, 2011, doi: 10.1016/j.mri.2011.06.001.

Wurnig, M.C. et al., "Systematic analysis of the intravoxel incoherent motion threshold separating perfusion and diffusion effects: Proposal of a standardized algorithm,"Magnetic Resonance Medicine, vol. 74, No. 5, pp. 1414-1422, 2014,. doi: 10.1002/mrm.25506.

Figure 1: An exemplary workflow of the DWI analysis method

Figure 2: An artificial DWI curve showing a mono-exponentially decaying form

Figure 3: An indicative artificial DWI curve exhibiting a bi-exponential decay form. By using the IVIM model and specific values for D, D*, and f, the true-diffusion coefficient decay curve (D) and the micro-perfusion coefficient (D*) decay curve are estimated Figure 4: Signal attenuation of each voxel of ROI_2 (gray curves) and their mean value (black curves with dots) as a function of b-values 0, 50, 100, 150, 200, 500, 1000, 1500 and 2000

Figure 5: Mean value of the signal intensities of ROI_2 (black dotted line) and the mean fitted signal attenuation decaying curve from the mono- and the bi-exponential model (dark gray and light gray curves respectively)

Figure 6: Mean value of the signal intensities of ROI_2 (black dotted line) and the estimated mean ADC, true-diffusion and micro-perfusion decaying curves (dark gray and light gray curves respectively)

Figure 7: Signal attenuation of each voxel of ROI_1 (gray curves) and their mean value (black curves with dots) as a function of b-values 0, 50, 100, 150, 200, 500, 1000, 1500 and 2000

Figure 8: Mean value of the signal intensities of ROI_1 (black dotted line) and the mean estimated signal attenuation from the mono- and the bi-exponential model (dark gray and light gray curves respectively)

Figure 9: Mean value of the signal intensities of ROI_1 (black dotted line) and the estimated mean ADC, true-diffusion and micro-perfusion decaying curves (dark gray and light gray curves respectively)

Figure 10: Bi-exponential decaying form of a voxel/ROI in the low b-value range

Figure 11: An exemplary flowchart of the Reduced b-values Incoherent Motion (REbIM) model Figure 12: Mean value of the signal intensities of ROI_2 (black dotted line) and the mean fitted signal attenuation decaying curve from the IVIM and the exemplary REbIM model (light gray and dark gray curves respectively)

Figure 13: Mean value of the signal intensities of ROI_2 (black dotted line) and the estimated mean true-diffusion and micro-perfusion decaying curves from the IVIM and the exemplary REbIM model (light gray and dark gray curves respectively)

Figure 14: Mean value of the signal intensities of ROI_2 (black dotted line) and the mean fitted signal attenuation decaying curve from the IVIM and the exemplary REbIM model (light gray and dark gray curves respectively) using less b-values in the low b-value range Figure 15: Mean value of the signal intensities of ROI_2 (black dotted line) and the estimated mean true-diffusion and micro-perfusion decaying curves from the IVIM and the exemplary REbIM model (light gray and dark gray curves respectively) using less b-values in the low b-value range Figure 16: Signal attenuation of each voxel of ROI_3 (gray curves) and their mean value (black curves with dots) as a function of b-values 0, 50, 100, 150, 200, 300, 600 and 1000

Figure 17: Mean value of the signal intensities of ROI_3 (black dotted line) and the mean fitted signal attenuation decaying curve from the IVIM and the exemplary REbIM model (light gray and dark gray curves respectively)

Figure 18: Mean value of the signal intensities of ROI_3 (black dotted line) and the estimated mean true-diffusion and micro-perfusion decaying curves from the IVIM and the exemplary REbIM model (light gray and dark gray curves respectively)

Figure 19: Mean value of the signal intensities of ROI_3 (black dotted line) and the mean fitted signal attenuation decaying curve from the IVIM and the exemplary REbIM model (light gray and dark gray curves respectively) using less b-values in the low b-value range Figure 20: Mean value of the signal intensities of ROI_3 (black dotted line) and the estimated mean true-diffusion and micro-perfusion decaying curves from the IVIM and the exemplary REbIM model (light gray and dark gray curves respectively) using less b-values in the low b-value range Figure 21: Snapshot of an exemplary computer implemented application for testing, evaluating and comparing the results of the exemplary REbIM model with the conventional approaches Figure 22: A workflow of the exemplary REbIM model, extended to the non-Gaussian diffusion

APPARATUSES, METHODS AND SYSTEMS FOR ESTIMATING WATER DIFFUSIVITY AND MICROCIRCULATION OF BLOOD USING DW-MRI DATA

CROSS REFERENCE TO RELATED APPLICATIONS

This application claims the benefit of U.S. Provisional Application No. 62/080,126, filed Nov. 14, 2014, which is incorporated by reference in its entirety as if fully set forth herein.

FIELD

The present subject matter is directed generally to apparatuses, methods, and systems for estimating parameters using Diffusion Weighted Magnetic Resonance Imaging (DW-MRI) data, and more particularly, to APPARATUSES, METHODS AND SYSTEMS FOR ESTIMATING WATER DIFFUSIVITY AND MICROCIRCULATION OF BLOOD USING DW-MRI DATA ("AEW").

RELATED ART

DW-MRI is an MRI technique reflecting at each voxel the rate of water diffusion at that location. DW-MRI is, therefore, a diagnostic noninvasive MRI technique based on the assessment of molecular diffusion of water in a tissue. Since the motion of water is influenced by the architecture of the cellular environment as well as thermal changes, certain pathological changes are known to be assessed by evaluating water diffusivity in the tissues with more sensitivity than traditional $T_1/T_2$ MRI.

DW-MRI relies on the spin-spin relaxation time ($T_2$ relaxation time), a time constant, which characterizes the magnetic-resonance-signal decay of the water protons. The general procedure to acquire DW-MRI data is to change the so-called "b-value", a quantity used for the identification of the measurement's sensitivity to DW-MRI. B-value is a measure of diffusion weighting that depends on the gyromagnetic ratio ($\gamma$), the amplitude of the diffusion gradient pulses (G), the duration of the pulses ($\delta$) and the time between the gradient pulses ($\Delta$). Also, apparent-diffusion-coefficient (ADC) is a well-known index that quantifies diffusion. DW-MRI data can, therefore, be acquired at different b-values. The formula below describes the relationship between b-values, signal intensity and ADC:

$$S_b = S_0 * \exp(-b*ADC) \quad (1)$$

where $S_b S_b$ is the signal intensity of the DW-MRI with a gradient factor attenuation b (s/mm$^2$), and $S_0$ is the measured signal intensity in the absence of diffusion weighting.

By altering the b-value, the signal of the DW-MRI is a function of the ADC (equation 1), showing a mono-exponential decay form (see FIG. 2) that can be estimated quantitatively with measurements on different b-values. Therefore, by fitting the mono-exponential model (i.e., linear fitting to the logarithmic scale of the signal intensities), the ADC at each voxel can be calculated.

With more than two b-values available, many studies have experimentally established that the DW-MRI signal attenuation as a function of the b-value cannot be well characterized by a mono-exponential model as the signal attenuation seems to also be influenced by the tissue microstructure, and thus the microcirculation of blood found in the capillary network. (see, e.g. Le Bihan, D., E. Breton, D. Lallemand, M. L. Aubin, J. Vignaud and M. Laval-Jeantet. 1988. Separation of diffusion and perfusion in intravoxel incoherent motion MR imaging. Radiology 168(2):497-505.) The intravoxel-incoherent-motion (IVIM) model addresses the effect of the microvasculature blood flow and the molecular diffusion of water in tissues in the DW-MRI signal of each voxel, which is described from the following bi-exponential equation (FIG. 3 is derived from this formula for D=1 mm$^2$/s, D*=100 mm$^2$/s and f=20%):

$$S_b = S_0 * ((1-f) * \exp(-b*D) + f * \exp(-b*D^*)) \quad (2)$$

The IVIM molecular diffusion coefficient D, the perfusion coefficient D*, and the fractional volume also known as perfusion fraction f, are derived for every voxel using non-linear fitting methods and then displayed as parametric maps. It is widely accepted that the molecular diffusion (D) and the perfusion coefficient (D*) differ at least an order of magnitude in the brain and more for other studied organs (D*/D>10). (see, Le Bihan, D. 2008. "Intravoxel incoherent motion perfusion MR imaging: a wake-up call." Radiology 249(3):748-752.) IVIM is an extended model of the conventional mono-exponential diffusion, which is reduced to a mono-exponential form in the absence of the perfusion fraction f. In this case, the diffusion coefficient D is the apparent diffusion coefficient (ADC, mm$^2$/s).

$$S_b = S_0 * \exp(-b*D) \quad (3)$$

In the range of low b-values (up to 300 s/mm$^2$), water molecules with high movement appear to contribute significantly to the diffusion signal whereas molecules with restricted movement activity play an important role in higher b-values (over 300 s/mm$^2$). From the biological standpoint, signal attenuation due to microvasculature blood flow (micro-perfusion or pseudo-diffusion effect) is mostly apparent at low b-values with their range varying depending on the tissue of interest. (see, Padhani, A. R., G. Liu, D. M. Koh, T. L. Chenevert, H. C. Thoeny, T. Takahara, A. Dzik-Jurasz, B. D. Ross, M. Van Cauteren, D. Collins, D. A. Hammoud, G. J. Rustin, B. Taouli and P. L. Choyke. (2009). Diffusion-weighted magnetic resonance imaging as a cancer biomarker: consensus and recommendations. Neoplasia 11(2): 102-125.) On the other hand, water diffusivity (true diffusion) is pronounced in higher b-values. (see, Yamada, I., W. Aung, Y. Himeno, T. Nakagawa and H. Shibuya. (1999). Diffusion coefficients in abdominal organs and hepatic lesions: evaluation with intravoxel incoherent motion echo-planar MR imaging. Radiology 210(3):617-623.) IVIM parameters estimation, as in the ADC estimation, is substantially affected by the presence of noise, especially in higher b-values. The DW-MRI signal follows an exponential decrease with increasing b-values, thus noise contamination is increased in high b-value images. The DW-MRI signal loss then becomes a limiting factor in diffusion analysis as it can easily be confused with the levels of noise, thus noise contamination to the DW-MRI signal is increased. (see, Dietrich O, Heiland S, Sartor K. (2001). Noise correction for the exact determination of apparent diffusion coefficients at low SNR. Magn Reson Med 45:448-453.)

Not using an IVIM model can result in erroneous estimation of quantitative diffusion parameters. For example, when using lower b-values (in the micro-perfusion range), and when capillary micro-perfusion is prominent (compared to the molecular diffusion component as in the case of liver), using solely the mono-exponential model results in ADC values that are higher than the true molecular diffusion coefficient D. On the other hand, when there is no significant micro-perfusion, D is comparable to ADC, which means that the mono-exponential model is adequate. However, IVIM has experimentally been shown to yield values, which deviate significantly from the range of the values for the D* and the perfusion fraction f as they appear in the literature and provided by several clinical studies.

Some other methods for increasing the signal-to-noise ratio (SNR) in DW images involve averaging the signal intensity over a Region of Interest (ROI), thus giving perfusion-related and diffusion-related IVIM measurements with low variance. But, averaging the DW signal over a ROI contributes to the loss of any heterogeneous information which may have occurred in the ROI such as necrotic and viable tumor areas. Some other methods for increasing the SNR involve the acquisition of multiple DW images and then use the averaged signal in a voxel-wise form to estimate the IVIM coefficients. However, this method increases the acquisition time and the time a patient needs to stay still until the end of the acquisition process.

The following references are related to the subject matter of AEW and, along with all of the literature referenced in this disclosure, are hereby incorporated by reference herein in their entirety:

Le Bihan, D., E. Breton, D. Lallemand, M. L. Aubin, J. Vignaud and M. Laval-Jeantet. 1988. Separation of diffusion and perfusion in intravoxel incoherent motion MR imaging. Radiology 168(2):497-505.

Padhani, A. R., G. Liu, D. M. Koh, T. L. Chenevert, H. C. Thoeny, T. Takahara, A. Dzik-Jurasz, B. D. Ross, M. Van Cauteren, D. Collins, D. A. Hammoud, G. J. Rustin, B. Taouli and P. L. Choyke. (2009). Diffusion-weighted magnetic resonance imaging as a cancer biomarker: consensus and recommendations. Neoplasia 11(2):102-125.

Yamada, I., W. Aung, Y. Himeno, T. Nakagawa and H. Shibuya. (1999). Diffusion coefficients in abdominal organs and hepatic lesions: evaluation with intravoxel incoherent motion echo-planar MR imaging. Radiology 210(3):617-623.

Dietrich O, Heiland S, Sartor K. (2001). Noise correction for the exact determination of apparent diffusion coefficients at low SNR. Magn Reson Med 45: 448-453.

Freiman M, Voss S D, Mulkern R V, Perez-Rossello J M, Callahan M J, Warfield S K. (2012). In vivo assessment of optimal b-value range for perfusion-insensitive apparent diffusion coefficient imaging. Med Phys. August 2012; 39(8):4832-9. doi: 10.1118/1.4736516.

Lemke, A., B. Stieltjes, L. R. Schad and F. B. Laun. (2011). Toward an optimal distribution of b values for intravoxel incoherent motion imaging. Magn Reson Imaging 29 (6):766-776.

Penner, A. H., A. M. Sprinkart, G. M. Kukuk, I. Gütgemann, J. Gieseke, H. H. Schild, W. A. Willinek and P. Mürtz. (2013). Intravoxel incoherent motion model-based liver lesion characterisation from three b-value diffusion-weighted MRI. Eur Radiol 23(10):2773-2783.

Zhang, J. L., E. E. Sigmund, H. Rusinek, H. Chandarana, P. Storey, Q. Chen and V. S. Lee. (2012). Optimization of b-value sampling for diffusion-weighted imaging of the kidney. Magn Reson Med 67(1):89-97.

http://clinical.netforum.healthcare.philips.com/global/Operate/Application-Tips/MRI/Tips-for-body-diffusion-weighted-imaging-%28DWI%29

SUMMARY

Both normal tissues and especially neoplasm regions in all organs of the human body and brain exhibit high structural and functional heterogeneity. Advanced medical imaging techniques such as DW-MRI are used for assessing qualitatively and quantitatively this complex environment. Several DW-MRI biomarkers are exported with the use of models such as the IVIM model describing tissue cellularity and microcirculation of blood in the capillary network.

A method for outputting an optimally modelled coefficient for a voxel in diffusion weighted magnetic resonance imaging, the method comprises (a) applying a mono-exponential model to signal intensities for a set of b-values at a particular voxel in a region of interest (ROI); (b) estimating a goodness of fit of the model applied in (a) by comparing the model to the signal intensities for b-values below a predetermined b-value at the particular voxel; (c) if the goodness of fit is less than a predetermined goodness threshold at the particular voxel, applying an intravoxel-incoherent-motion (IVIM) model to the signal intensities for the set of b-values at the particular voxel and determining a perfusion fraction parameter (f), true-diffusion coefficient (D) and micro-perfusion coefficient (D*) using the IVIM model; (d) outputting an apparent diffusion coefficient (ADC) determined from the mono-exponential model for the particular voxel, if (i) the goodness of fit is not less than the predetermined goodness threshold, (ii) if f is equal to a lower bound of a predetermined fraction range used in applying the IVIM model in (c), or (iii) D*/D is less than 10; and (e) outputting the true diffusion (D) determined from the IVIM model for the particular voxel, if (i) the goodness of fit is less than the predetermined goodness threshold, (ii) f is not equal to the lower bound of the predetermined fraction range used in applying the IVIM model in (c), and (iii) D*/D is not less than 10.

In another aspect, step (b) comprises (b1) determining an R-square coefficient ($R^2$) between the mono-exponential model and the signal intensities for the set of b-values at the particular voxel according to the formula $$R^2 = 1 - SS_{res}/SS_{tot}$$

where $SS_{res}$ is a residual sum of squares and $SS_{tot}$ is a total sum of squares; (b2) determining an adjusted-$R^2$ coefficient according to the formula $$\text{adjusted } R^2 = 1 - (1-R^2)*(n-1)/n-p-1$$

where n is the number of b-values used and p is the number of parameters used from the mono-exponential model; and (b3) outputting the adjusted-$R^2$ coefficient as a measure of the goodness of fit.

In another aspect, step (b) comprises determining a root-mean-square error (RMSE) between the mono-exponential model and the signal intensities for the set of b-values at the particular voxel and outputting the RMSE as a measure of the goodness of fit.

In another aspect, steps (a) through (e) are repeated for a plurality of voxels in the ROI.

In another aspect, the method further comprises generating a map for each voxel in the ROI indicating whether the ADC or the true diffusion was output at steps (d) and (e), respectively.

In another aspect, the predetermined b-value is 300 s/mm$^2$.

In another aspect, the set of b-values includes five or fewer b-values.

In another embodiment, a method for modeling a portion of a diffusion weighted magnetic resonance image, the method comprises (a) determining a perfusion fraction parameter (f), micro-perfusion coefficient (D*) and adjusted slope (α) using a non-linear least-squares fitting technique to fit the formula $$S_{low\_b}=S_0*(-a*b+(1-f)+f*\exp(-b*D^*))$$

to signal intensities at a particular voxel in a region of interest (ROI) for at least three b-values below a predetermined b-value threshold; (b) using f, D* and a determined in step (a), to determine a true-diffusion coefficient (D); and (c) determining a signal attenuation $S_b$ for a b-value greater than the predetermined b-value threshold using D determined in step (b) and the formula $$S_b=S_{0\_diffusion}*\exp(-b*D)$$

where $S_{0\_diffusion}$ is the signal intensity of true-diffusion at b=0.

In another aspect, the method further comprises (d) using D determined in step (b) to determine a kurtosis coefficient $K_{app}$ from the formula:

$$S_b=S_0*\exp(-b*D+1/6*b^2*D^2*K_{app}).$$

In another aspect, the method further comprises repeating steps (a) through (d) for a plurality of voxels in the ROI.

In another aspect, the method further comprises (e) comparing $K_{app}$ determined in step (d) for each voxel to a low kurtosis threshold and a high kurtosis threshold; and (f) generating a classification map for each voxel in the ROI indicating whether $K_{app}=0$, whether $K_{app}$ is less than the low kurtosis threshold or whether $K_{app}$ is greater than the high kurtosis threshold.

BRIEF DESCRIPTION OF THE DRAWINGS

The accompanying drawings illustrate various non-limiting, example, inventive aspects in accordance with the present subject matter.

Figure 1:
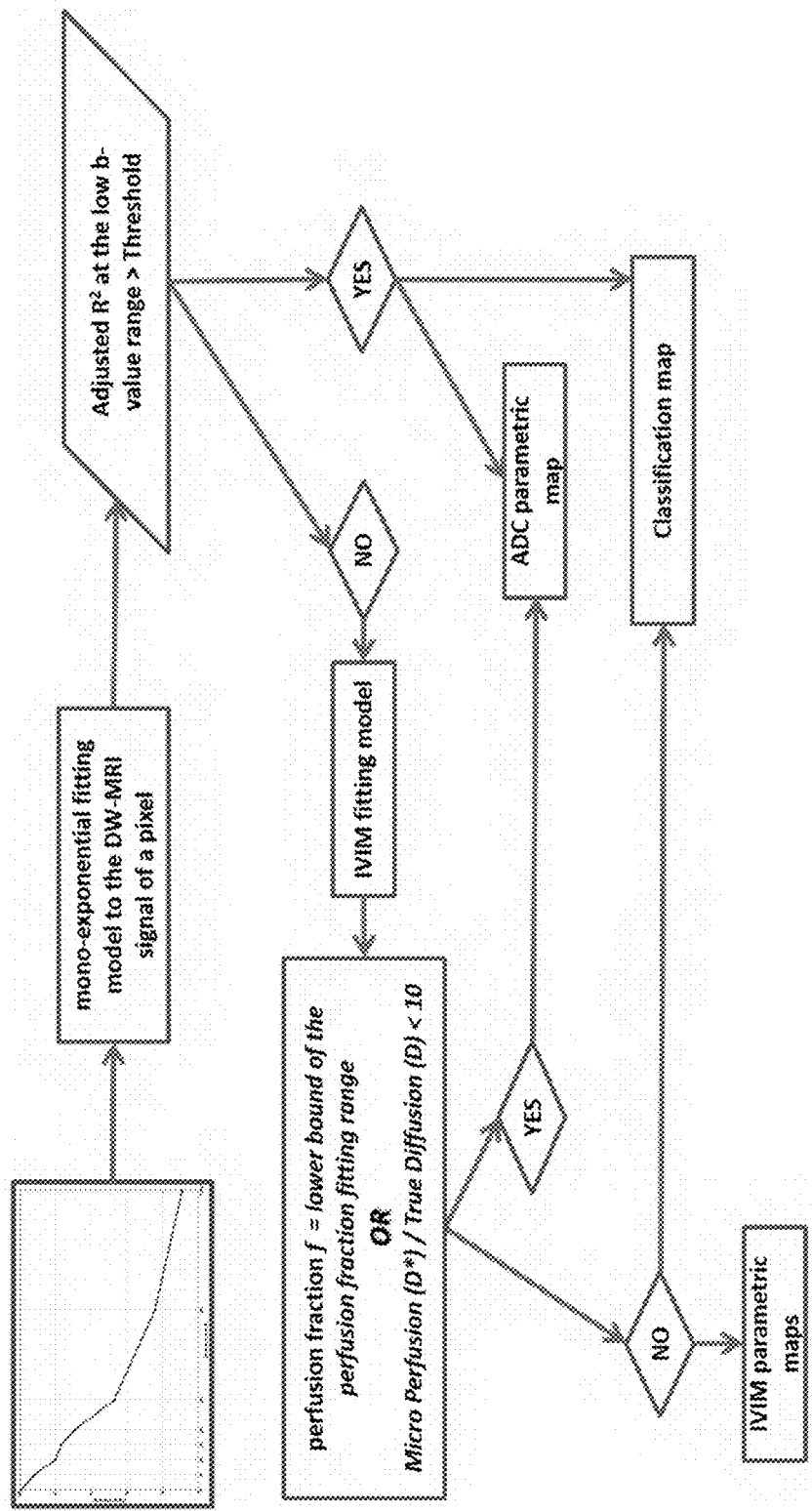
FIG. 1 is an exemplary workflow of the DWI analysis method, according to an implementation of the present subject matter.

The leading number of each reference number within the drawings indicates the figure in which that reference number is introduced and/or detailed. As such, a detailed discussion of reference number 101 would be found and/or introduced in FIG. 1. Reference number 201 is introduced in FIG. 2, etc.

It should be appreciated by those skilled in the art that any block diagrams herein represent conceptual views of illustrative systems. Similarly, it should be appreciated that any flow charts, flow diagrams, state transition diagrams, pseudo code, and the like represent various processes, which may be substantially represented in a computer readable medium and so executed by a computer or processor, whether or not such computer or processor is explicitly shown.

The order in which both the various methods described herein is not intended to be construed as a limitation, and any number of the described method steps can be combined in any order to implement the methods, or an alternative method. Additionally, individual steps may be deleted from or added to the methods described herein without departing from the spirit and scope of the subject matter described herein. Furthermore, the methods can be implemented in any suitable hardware, software, firmware, or combination thereof. The methods may also be taught to a user through written, pictographic, audio or audiovisual instructions.

DETAILED DESCRIPTION

Since it is impossible to assess a priori the actual micro-perfusion effect corresponding to each voxel, using solely mono-exponential or IVIM on the entire image will unavoidably lead to errors. To this end, embodiments of AEW disclose a system and a method for identifying whether a voxel or a region of a DW-MRI exhibits micro-perfusion activity or not, and uses the appropriate analysis model to compute quantitative diffusion parameters in this voxel/region.

Embodiments of AEW offers solutions to many issues with traditional approaches. For example, none of the traditional approaches define an accurate metric that classifies voxels to those showing either a mono-exponential decaying form and requiring ADC analysis, or a bi-exponential decaying form where IVIM is required. Neither ADC nor IVIM parameter estimation can be a generic solution for every voxel in a region of interest (ROI) at any anatomical region. Therefore, in one implementation, a classification coefficient is determined in order to assign the appropriate model to each voxel or region to better account for the micro perfusion activity.

Also, selecting appropriate b-values for estimating the perfusion and diffusion effect using the IVIM model can be a trade-off in the imaging process that needs an adequate balance between the maximum selected b-value and the resulting levels of image noise. (see, Lemke, A., B. Stieltjes, L. R. Schad and F. B. Laun. (2011). Toward an optimal distribution of b values for intravoxel incoherent motion imaging. Magn Reson Imaging 29(6):766-776.) On one hand, both high and low b-values are used in order to provide enough signal contrast. On the other hand, in higher b-values, the acquired signal is highly contaminated with noise resulting to very low Signal to Noise Ratio (SNR).

To address at least the foregoing issues, embodiments of AEW present an exemplary Reduced b-values Incoherent Motion (REbIM) model that, in one implementation, only requires b-values from the low b-value range (typically <300 s/mm$^2$). In one implementation, this can be achieved by applying a goodness of fit coefficient to the low b-value range and assign accurately the appropriate diffusion analysis model, either mono-exponential in the absence of micro-perfusion or bi-exponential (IVIM) taking into consideration microvasculature blood flow, in each voxel of a selected ROI.

AEW offers various advantages over traditional approaches including, but not limited to:
a) avoiding getting signal from high b-values, which are affected by low SNR (and often need acquiring multiple DW-MRIs in high b-values to improve SNR) by using DW-MRI signal attenuation only from low b-values for performing IVIM diffusion analysis;
b) reduction of the acquisition time and patient discomfort by using fewer b-values than required by the IVIM model for estimating D, D* and f;
c) the ability to generate synthetic DW-MRI data at high b-values based on the exemplary IVIM model's equation; and
d) the ability to also estimate non-Gaussian diffusion parameter $K_{app}$ with less b-values.

The present subject matter provides a computational framework of choosing and applying the most appropriate model in different regions of a heterogeneous area. Specifically, this framework supports the simultaneous use of more than one model in a single analysis and selects which one is statistically the more precise on a voxel-by-voxel basis. This is very important, for example, in the presence of lesions with increased heterogeneity where a single model fails to fit accurately in all tumor areas (necrotic areas show typically a mono-exponential decaying form in their signal, whereas hyper-vascular areas are characterized by bi-exponentially decaying signals as a function of their b-values).

This subject matter allows the computation of true diffusion (D), micro-perfusion (D*) and perfusion fraction (f) with the presented REbIM model.

The REbIM model requires only 3-5 b-values in contrast to conventional methods that need 6-8 b-values which means that less scanning time is needed to acquire the DWI-MRI sequences.

This subject matter can therefore decrease the scanning time necessary for computing the D, D* and f parameters. This is achieved in the basis of reduced number of b-values need to be acquired (6 to 8 is typically necessary when utilizing conventional fitting methods as opposed to 3-5 needed when using this exemplary model).

The necessary scanning time is further decreased due to the fact that the low b-values that will be acquired for REbIM (in the range of 0-300), are rich in terms of Signal to Noise Ratio (SNR) and therefore fewer averages need to be acquired as opposed to the standard b-values schemes. In conventional bi-exponential fitting methods where b-values in the range of (300+) are needed, high b-value images are poor in terms of SNR and therefore multiple averages need to be acquired for these images further increasing the scanning time.

Furthermore, the reduced number of b-values results in better fitting accuracy due to the lower possibility of motion-related artifacts. This is particularly important for non-cooperative patients and pediatric applications (e.g. oncology).

REbIM also extends to non-Gaussian diffusion where along with the bi-exponential behavior of the diffusion signals, very high b-values (more than 1000) reveal deviations from non-Gaussian behaviors that are quantitatively assessed with the Kurtosis coefficient K. The extended REbIM model computes K with the use of less b values, i.e. without b-values in the range of 300-1000 which are necessary in the non-Gaussian model referenced in the application which combines the IVIM and the DKI model. The application of the extended REbIM model for estimating D, D*, f and K therefore leads to a reduction in the necessary scanning time.

AEW can also be used in software that quantifies DW-MRI data as discussed in the following paragraphs. The description and figures merely illustrate exemplary embodiments of the AEW. It will thus be appreciated that those skilled in the art will be able to devise various arrangements that, although not explicitly described or shown herein, embody the principles of AEW. Furthermore, all examples recited herein are intended to be for pedagogical purposes only to aid the reader in understanding the principles of AEW and the concepts contributed by the inventor(s) to furthering the art, and are to be construed as being without limitation to such specifically recited examples and conditions.

AEW finds applications in DW-MRI of tissues, for example, benign and malign tumors in tissues such as soft tissues, e.g., breast tissue. It is noted that, while a particular application directed to analysis of lesions in liver MRI may be shown, the description is not limited to the specific embodiment illustrated. AEW may find applications with respect to other types of anatomical sites, such as the brain, prostate, kidney and breast. Furthermore, the methods and systems described herein can be used to detect pathologies, such as stroke, chronic brain ischemia, cancer, liver cirrhosis, etc. Moreover, all statements herein reciting principles, aspects, and embodiments of AEW, as well as specific examples thereof, are intended to encompass equivalents thereof.

Figure 2:
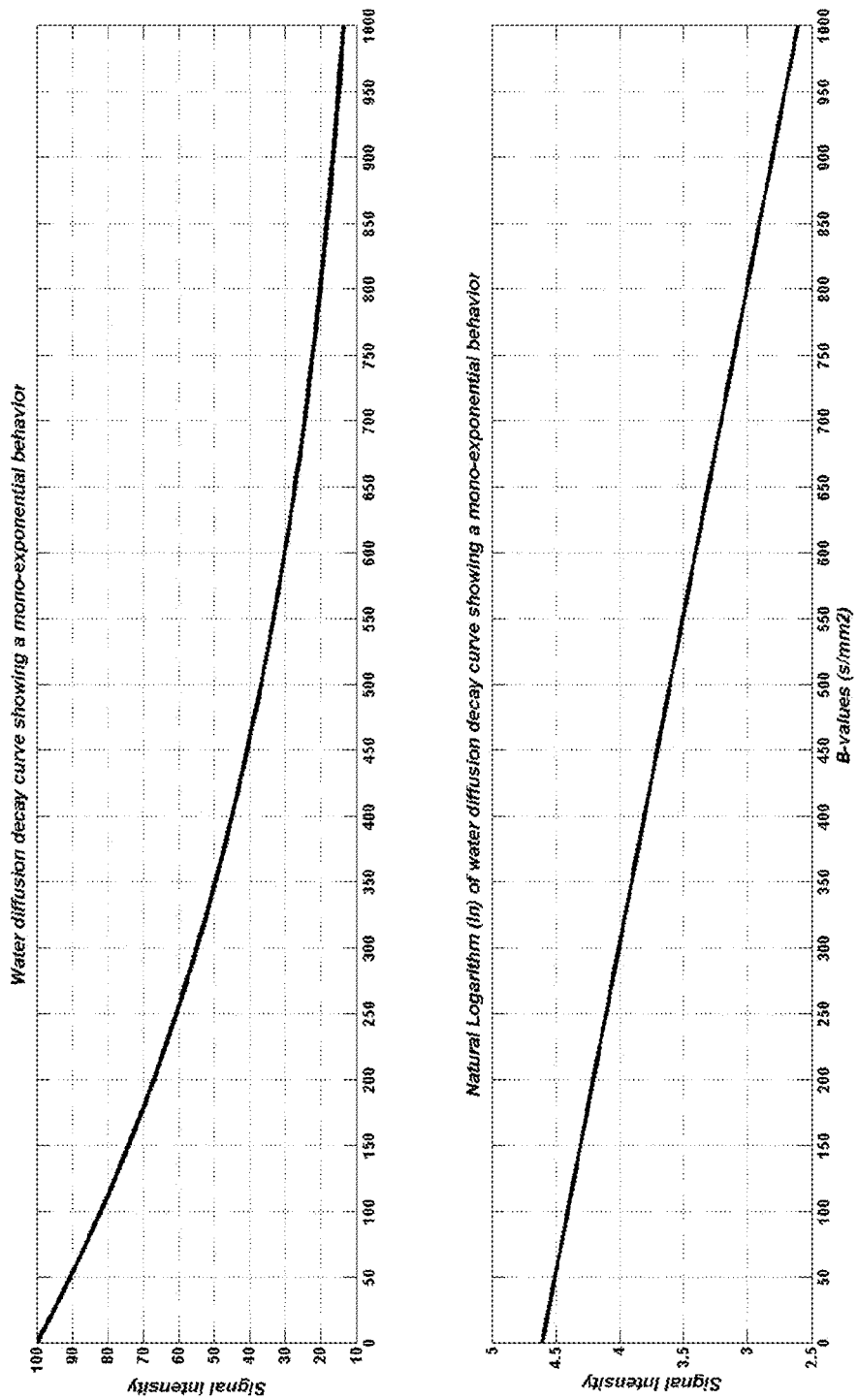
FIG. 2 is an artificial DWI curve showing a mono-exponentially decaying form, according to an embodiment of the current subject matter.
Figure 3:
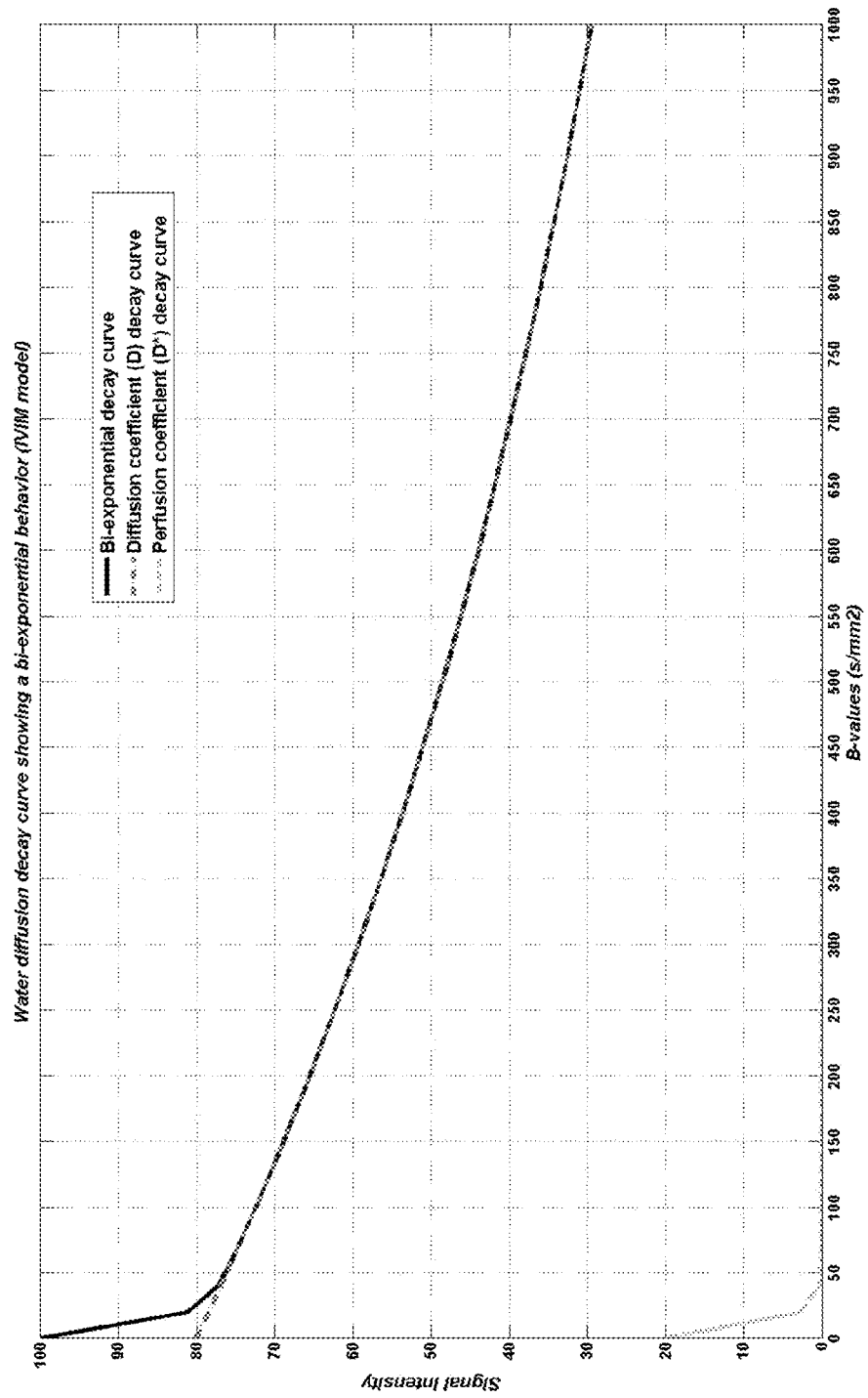
FIG. 3 is an indicative artificial DWI curve exhibiting a bi-exponential decay form. By using the IVIM model and specific values for D, D*, and f, the true-diffusion coefficient decay curve (D) and the micro-perfusion coefficient (D*) decay curve are estimated, according to an embodiment of the current subject matter.

FIG. 1 is an exemplary flowchart of the method implemented for obtaining classification maps, ADC parametric maps, and IVIM parametric maps, according to an implementation. In one implementation, an exemplary method is applied to define the goodness of fit of mono and bi exponential models and assign the best model for each voxel, for example, by using an adjusted R-square coefficient ($R^2$) as a classification coefficient. To show the effectiveness of the exemplary method, both mono- and IVIM models were applied to several clinical data from different anatomical regions and indicative diffusion analysis, the results of which are shown in FIG. 4 to FIG. 9. As per one implementation, the exemplary method includes the following steps:

In one implementation, the mono-exponential model (ADC estimation) is applied to each voxel of the ROI using signals from a set of b-values. For example, in one implementation, the set of b-values may include all available b-values.

In one implementation, the goodness of fit is estimated, for example, only at low b-values (<300 s/mm$^2$). If the goodness of the mono-exponential model fit (given by adjusted $R^2$ as described below) is higher than a threshold (typically 90% but can be defined by the user), the examined voxel is assumed to follow mono-exponential behavior and to lack micro-perfusion activity. In this case, ADC is the suitable quantitative diffusion parameter.

If not, then the IVIM model is applied to the voxel at, for example, all b-values and D, D* and f is computed.

In one implementation, the clinical relevance, that may vary for each organ examined, of the perfusion fraction parameter f, is examined. If its value is equal to the lower bound of this range, the voxel can be assumed to follow mono-exponential behavior and to lack any significant micro-perfusion activity. In addition, if D*/D<10 the voxel can be assumed to follow mono-exponential behavior. In all other cases, it can be assumed to follow bi-exponential behavior and the IVIM model can be used. In this case the molecular diffusion can be quantified by the true-diffusion (D).

In one implementation, the corresponding pseudo-colored maps (ADC, D, D*,f) can be generated for each voxel in the ROI. A classification map that separates the voxels in two classes, one exhibiting mono-exponential and one bi-exponential behavior can also be produced.

In order to assess the goodness of fit from both models to the DW-MRI data, a statistical coefficient from regression analysis named adjusted R-square ($R^2$) can be applied. $R^2$ is used as a coefficient to indicate how well the modeled data (from mono-exponential, bi-exponential models) fit the raw data (DW-MRI signal intensity as a function of b-values). $R^2$ is given by:

$$R^2 = 1 - SS_{res}/SS_{tot}$$

where $SS_{res}$ is the residual sum of squares and $SS_{tot}$ is the total sum of squares. $R^2$ ranges from 0 to 1 with 1 indicating perfect fitting. $R^2$ is precision-sensitive in the sense that when the number of b-values increases the $R^2$ increases even if the fitting accuracy remains constant. To address this, selected value of the adjusted-$R^2$ can be very similar metric to $R^2$ in some ways, but can differ from $R^2$ in that $R^2$ is unbiased to the number of the b-values used. The adjusted-$R^2$ may be given by the following formula where n is the number of the b-values used and p the number of the parameters from each model.

$$\text{adjusted } R^2 = 1 - (1-R^2)*(n-1)/n-p-1$$

Figure 4:
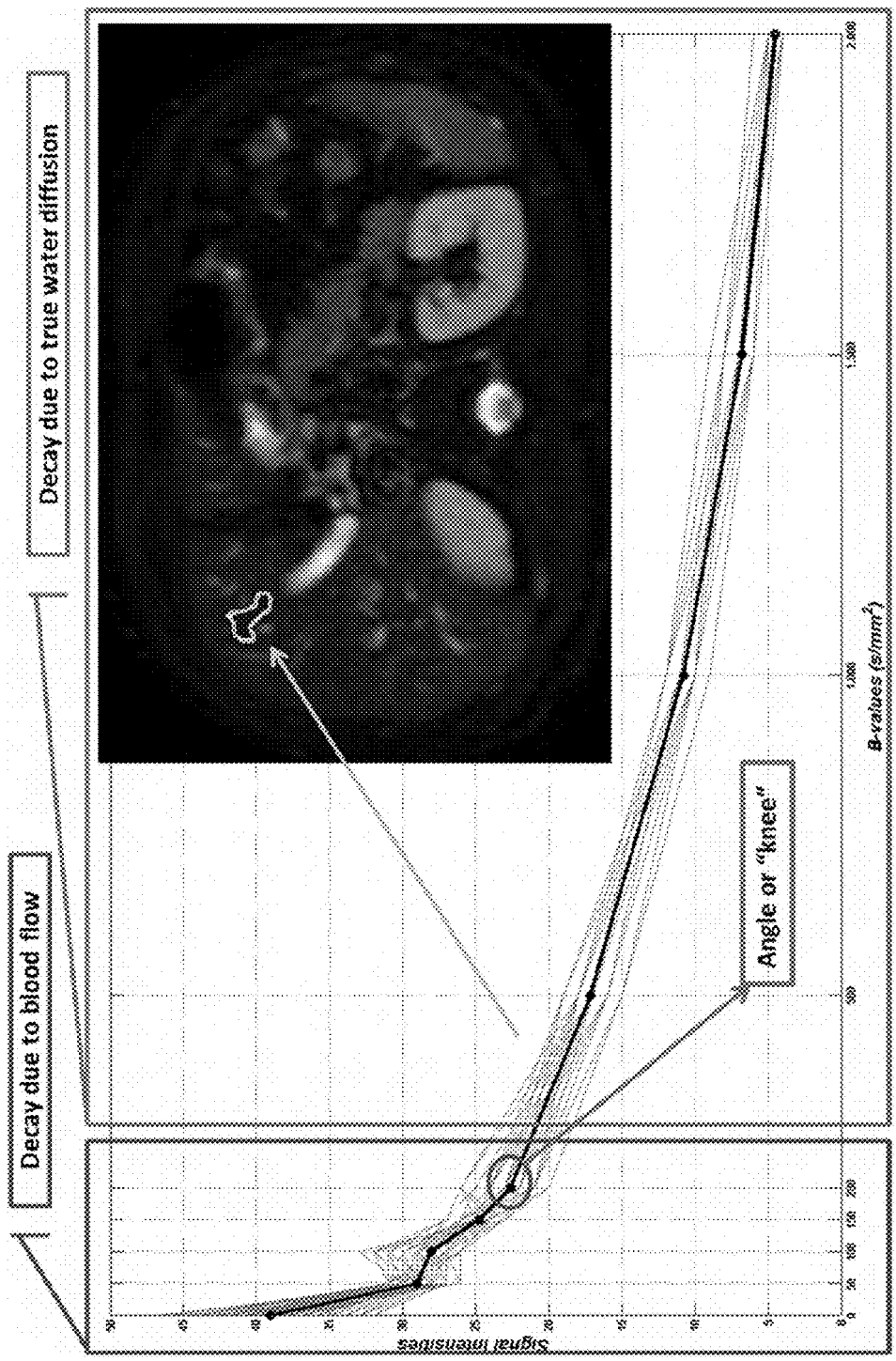
FIG. 4 is a graphical representation of signal attenuation of each voxel of ROI_2 (gray curves) and their mean value (black curves with dots) as a function of b-values 0, 50, 100, 150, 200, 500, 1000, 1500 and 2000, according to an embodiment of the current subject matter.
Figure 7:
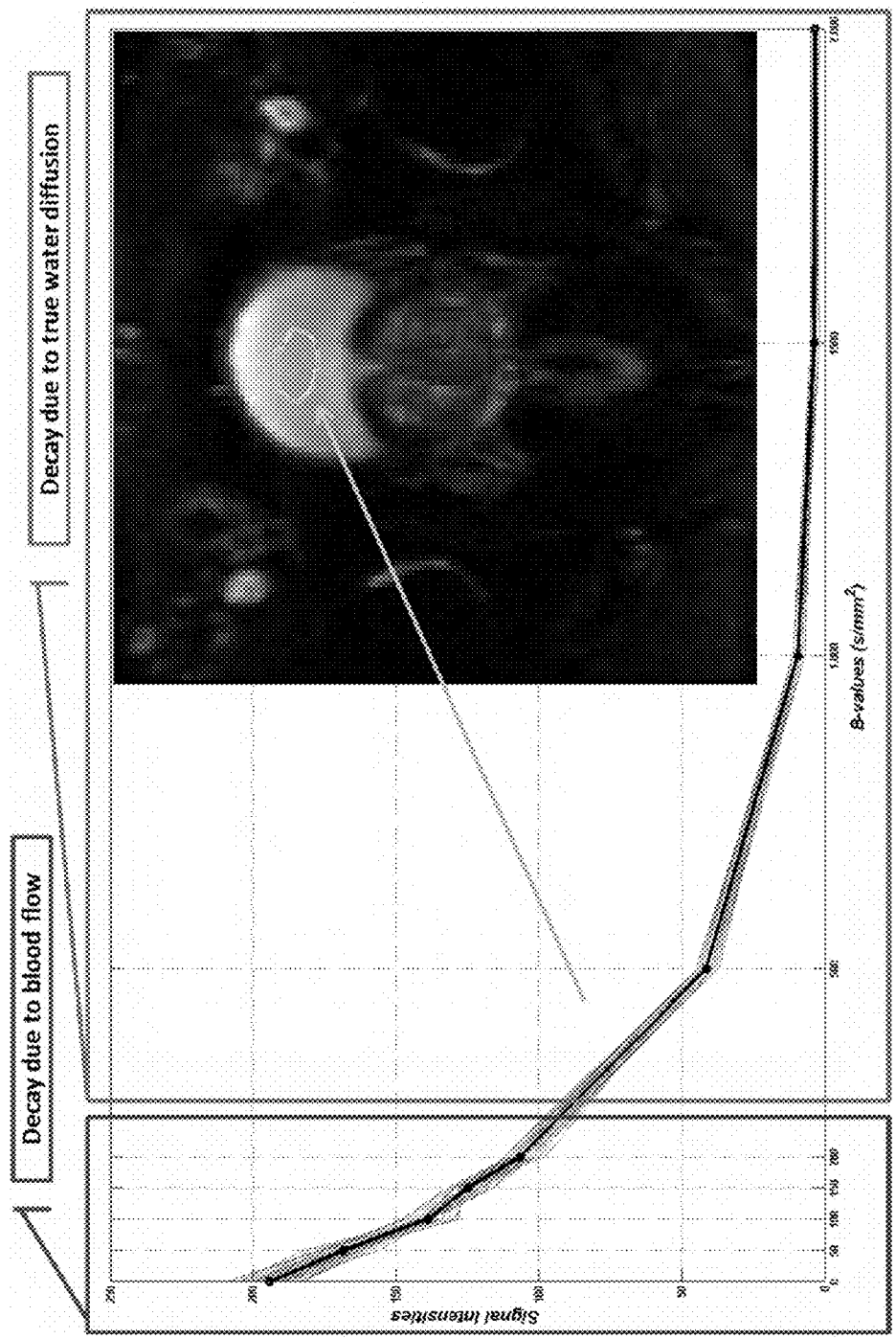
FIG. 7 is a graphical representation of signal attenuation of each voxel of ROI_1 (gray curves) and their mean value (black curves with dots) as a function of b-values 0, 50, 100, 150, 200, 500, 1000, 1500 and 2000, according to an implementation of the present subject matter.

In one implementation, to illustrate the use and value of the exemplary method, two different ROIs with distinct morphological characteristics were selected: a ROI (named as ROI_1) from an anatomical area with known absence of micro-perfusion effect (showing a mono-exponential decaying form as seen in FIG. 7), and a ROI (named as ROI_2) with a known high degree of blood microcirculation (showing a bi-exponential decaying form as seen in FIG. 4).

Figure 5:
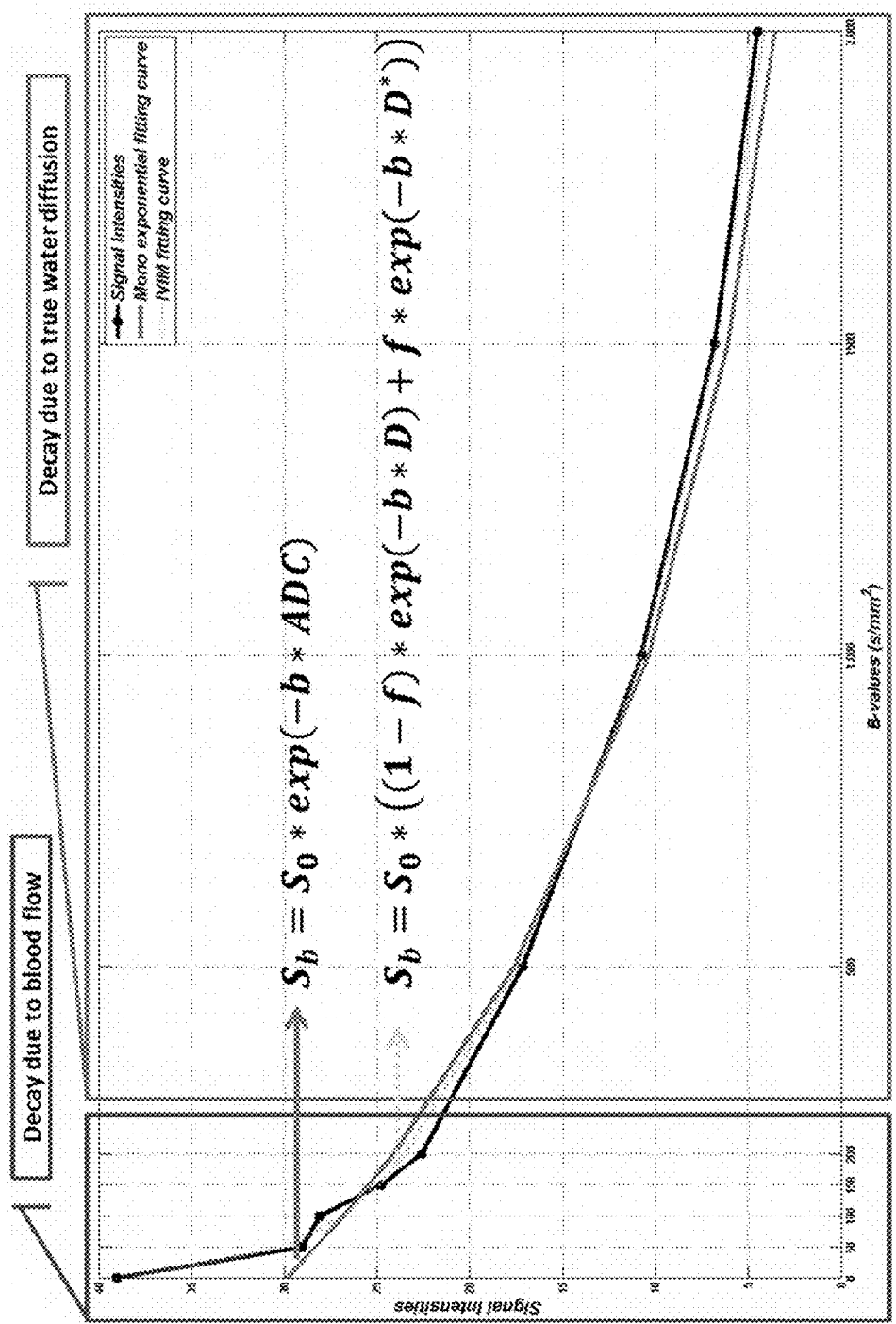
FIG. 5 is a graphical representation of mean value of the signal intensities of ROI_2 (black dotted line) and the mean fitted signal attenuation decaying curve from the mono- and the bi-exponential model (dark gray and light gray curves respectively), according to an embodiment of the current subject matter.
Figure 6:
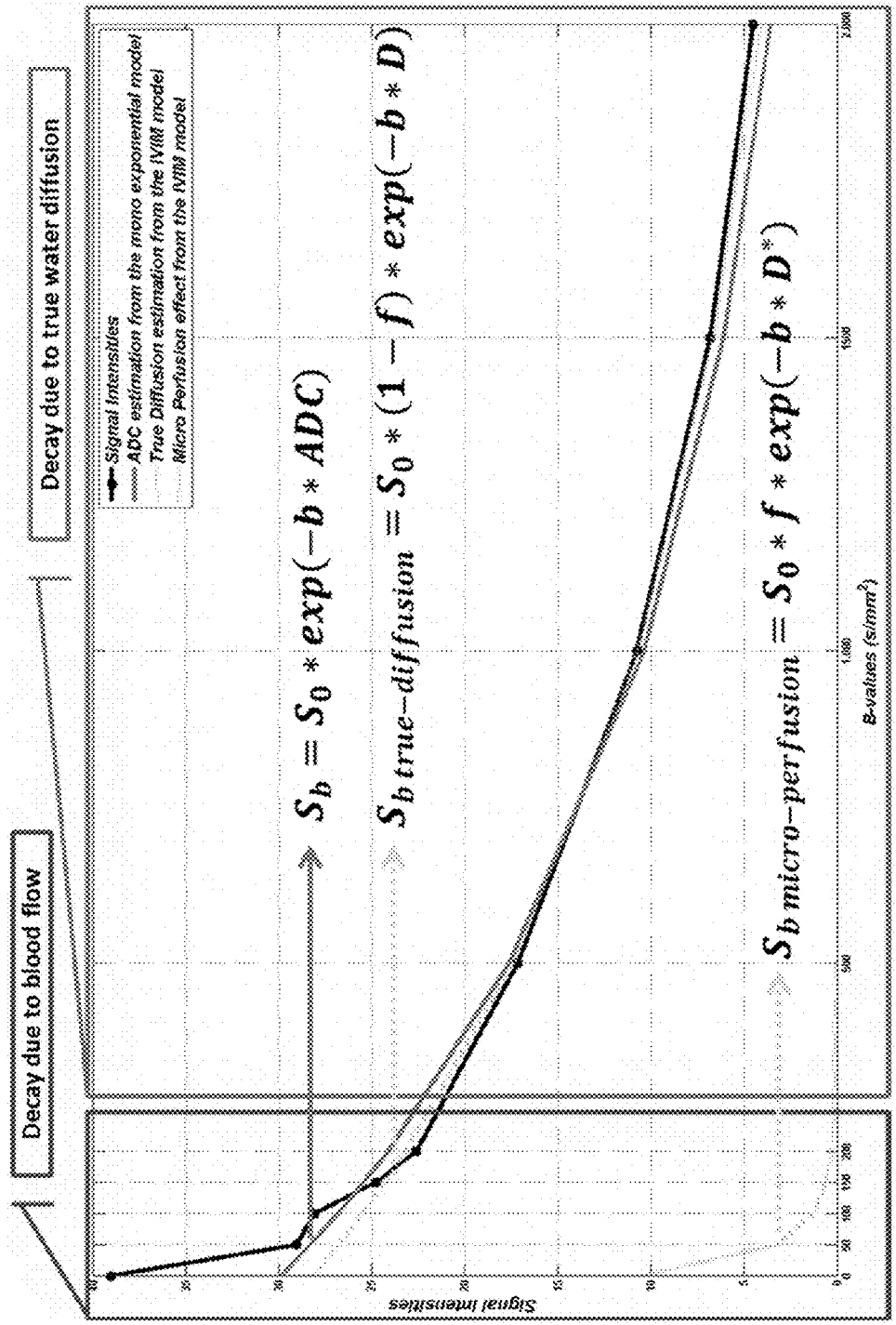
FIG. 6 is a graphical representation of mean value of the signal intensities of ROI_2 (black dotted line) and the estimated mean ADC, true-diffusion and micro-perfusion decaying curves (dark gray and light gray curves respectively), according to an implementation of the present subject matter.
Figure 8:
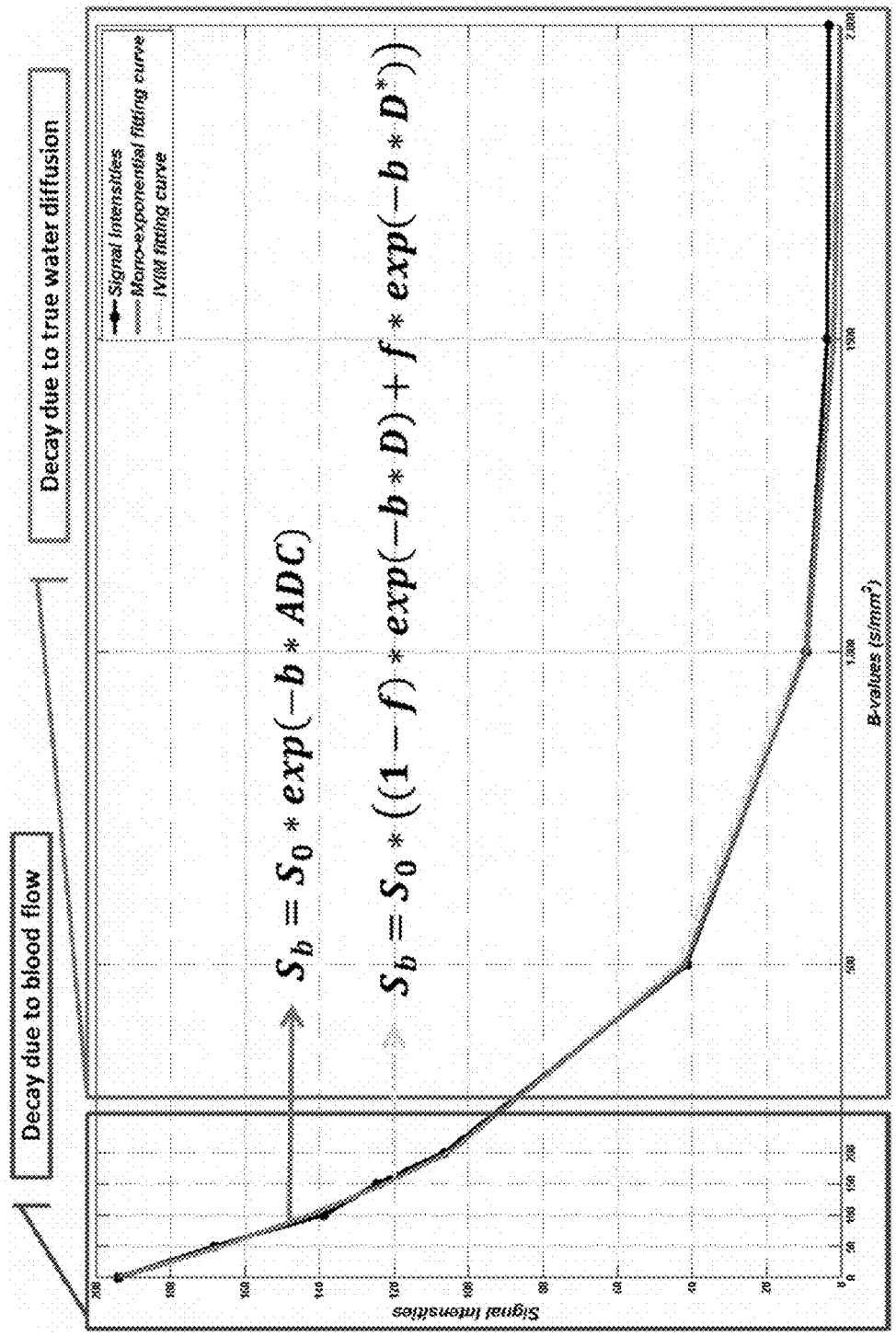
FIG. 8 is a graphical representation of mean value of the signal intensities of ROI_1 (black dotted line) and the mean estimated signal attenuation from the mono- and the bi-exponential model (dark gray and light gray curves respectively), according to an implementation of the present subject matter.
Figure 9:
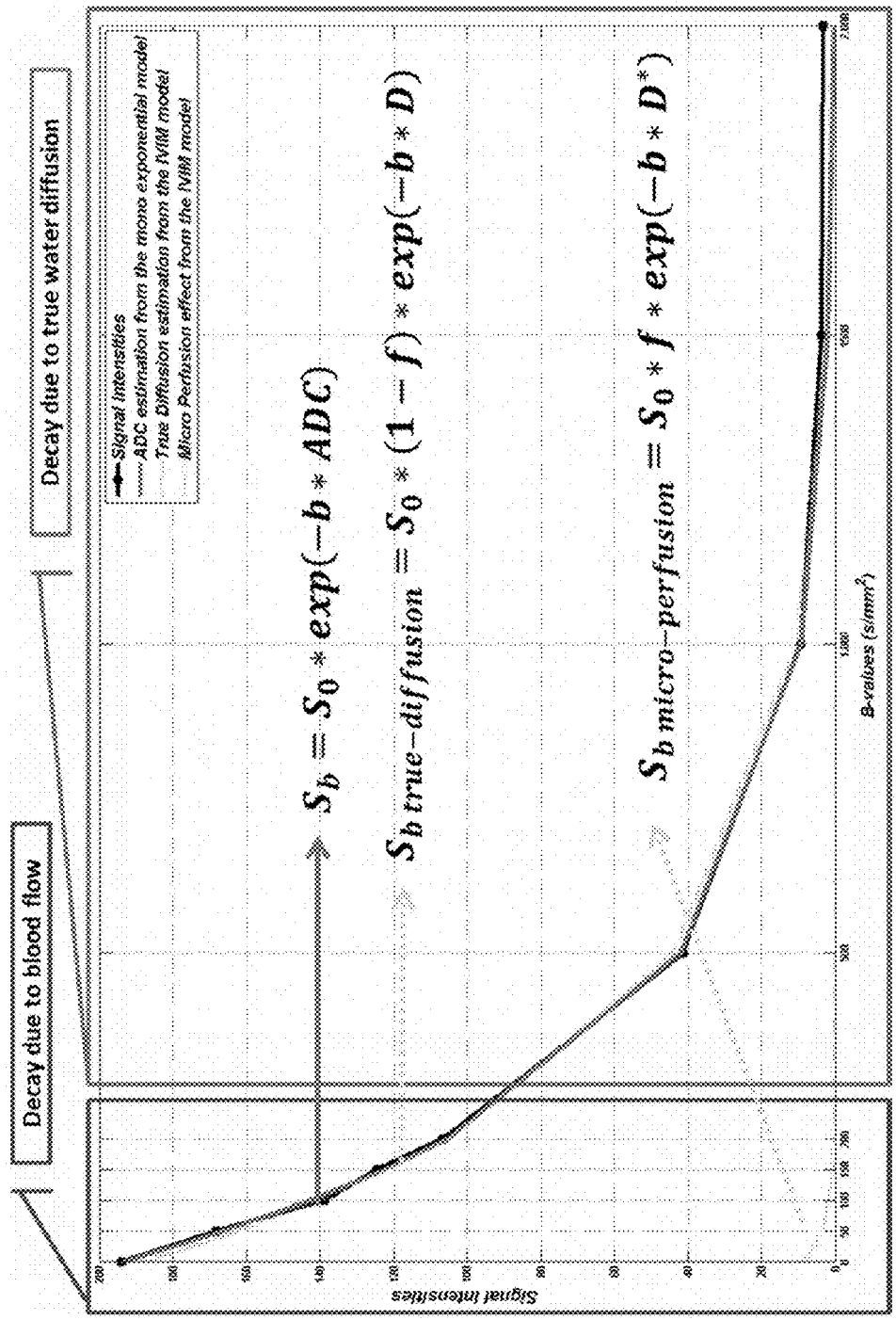
FIG. 9 is a graphical representation of mean value of the signal intensities of ROI_1 (black dotted line) and the estimated mean ADC, true-diffusion and micro-perfusion decaying curves (dark gray and light gray curves respectively), according to an implementation of the present subject matter.

The following analysis for the ROIs shows that when using ADC or IVIM parameters, for example, for characterizing the diffusivity, there may be errors (especially in ROIs containing heterogeneous tissues), even if models are well-fitted to data. Therefore, in these two ROIs, the following analyses was performed:

a) mono- (ADC parameter estimation) and bi-exponential (IVIM) models were sequentially applied at each voxel in both ROIs using a nonlinear least-square fitting method for estimating ADC and D, D* and f respectively.

b) Then, following a reverse engineering approach, the model signal intensities $S_b$ of each voxel from the mono and bi-exponential models computed (building synthetic DW-MRI data at each b-value from the mono- and bi-exponential equations).

c) The mean fitted signal $S_b$ from all voxels in the ROI was estimated using each model and plotted together with the mean value of the raw DW-MRI signal intensities of each ROI (see FIG. 5 and FIG. 8).

d) Also, mean values of $S_{b\ micro\text{-}perfusion}$ and $S_{b\ true\text{-}diffusion}$ (synthetic data from the equations below), were plotted in the same graph as the DW-MRI signal (see FIG. 6 and FIG. 9). Both equations are part of the bi-exponential model (IVIM).

$$S_{b\ micro\text{-}perfusion} = S_0 * f * \exp(-b*D^*)$$

$$S_{b\ true\text{-}diffusion} = S_0 * (1-f) * \exp(-b*D)$$

In one implementation, by using these analysis steps, the two different hypotheses can be tested:

a) the mono-exponential model can provide accurate diffusion parameters in all cases; and b) the bi-exponential model can provide accurate diffusion parameters in all cases.

To test hypothesis (a), a specific region in the liver parenchyma with excluded visible vessels was defined (ROI_2) to ensure that micro-perfusion effect was substantially significant. Parametric maps for the ADC, D, D* and f were estimated in every voxel of the ROI with the assumption that the mono-exponential model (yielding ADC) is the appropriate diffusion model. The anatomical area of the DW-MRI and the signal intensities of each voxel of ROI_2 (light gray lines) are depicted in FIG. 4. The mean DW-MRI signal intensities of ROI_2 are also plotted by a thick black dotted line in the same figure.

The b-values axis was separated, according to the theory, into two distinct regions; the low b-value where the signal attenuation decay is caused due to micro-perfusion (up to 300 s/mm² indicated by a red box) and the high b-value where signal is affected by true molecular diffusion (over 300 s/mm² indicated by a blue box).

The conclusions derived from the first part of the analysis (see FIG. 5, FIG. 6 and Table 1) are:

The ADC from the mono-exponential model is higher than experimentally provided by the literature ADC range in DW-MRI protocols with maximum b-value equals to 2000 s/mm². (see, Koh, D. M., D. J. Collins and M. R. Orton. 2011. "Intravoxel incoherent motion in body diffusion-weighted MRI: reality and challenges." AJR Am J Roentgenol 196(6):1351-1361.)

The IVIM model seems to correctly calculate the diffusivity of the voxels in ROI_2 (diffusion parameters falling in the ranges as they appear in the clinical studies provided in the literature). (see, Dijkstra, H., P. Baron, P. Kappert, M. Oudkerk and P. E. Sijens. 2012. "Effects of microperfusion in hepatic diffusion weighted imaging." Eur Radiol 22(4): 891-899.)

The mono-exponential model shows a high adjusted-$R^2$ (>90%) if applied to the overall b-value range (from 0 to 2000 s/mm²), but is lower when compared to the IVIM fitting curve (see Table 1).

The adjusted-$R^2$ from both the mono- and the bi-exponential model is high when applied, for example, only to the high b-value area (>97%) confirming that this area exhibits a mono-exponential decaying form (true diffusion is the dominant phenomenon).

There is a significant difference in the adjusted-$R^2$ between the mono- and the bi-exponential model when applied, for example, only to the low b-value range (see Table 1). The adjusted-$R^2$% difference between the two models rises up from ~8% to more than 22% giving a clear indication that IVIM is the right model for a good classification.

In conclusion, the mono-exponential model does not yield clinically correct value for the diffusion parameters in ROI_2 since it does not fall in the range reported in the literature (using the overall adjusted-$R^2$ as the classification indicator). Going back to FIG. 1, it will be understood that even a strict threshold of 90% to the adjusted-$R^2$ would fail giving a good classification for the voxels in ROI_2.

To test hypothesis (b) the analysis was performed in ROI_1 (see FIG. 7). The IVIM model was applied to each voxel of the ROI and the results of the analysis are displayed in FIG. 8 and FIG. 9. ADC diffusion analysis has been also performed and the results are presented in Table 2.

TABLE 1

Quantitative representation of the DWI analysis for ROI_2

|  | ADC/True Diffusion (D) | Overall Adjusted $R^2$ | Adjusted $R^2$ low b-value area | Adjusted $R^2$ high b-value area | Adjusted $R^2$ % difference | Adjusted $R^2$ low b-value % difference | Adjusted $R^2$ high b-value % difference |
|---|---|---|---|---|---|---|---|
| Mono-exponential | $1.6*10^{-3}$ | 91.60% | 75.99% | 97.72% | 7.75% | 22.12% | ~0% |
| IVIM | $1*10^{-3}$ | 99.29% | 97.57% | 97.70% | | | |

TABLE 2

Quantitative representation of the DWI analysis for ROI_1
(Adj. is for Adjusted)

| | ADC/True Diffusion (D) mean value | Perfusion Fraction (f) mean value | Micro Perfusion (D*) mean value | Adj. $R^2$ mean value | Adj. $R^2$ low b-value area | Adj. $R^2$ high b-value area | Adj. $R^2$ % difference | Adj. $R^2$ low b-value % difference | Adj. $R^2$ high b-value % difference |
|---|---|---|---|---|---|---|---|---|---|
| Mono-exponential | $3.1*10^{-3}$ | — | — | 99.40% | 99.34% | 93.51% | ~0% | ~0% | ~0% |
| IVIM | $3*10^{-3}$ | 2.22% | $7.4*10^{-3}$ | 99.79% | 99.36% | 92.81% | | | |

Despite the fact that based on the overall adjusted-$R^2$, IVIM perform better than the mono-exponential model, the estimated ratio of true diffusion (D) and micro-perfusion (D*) is less than 10 indicating mono-exponential behavior for this specific ROI. In this particular ROI, D=$7.4*10^{-3}$ (see Table 2). Therefore, said second hypothesis is false.

Based on the above observations, the exemplary methods described herein estimate the goodness of fit at various levels, for example, at low b-values (<300 s/mm$^2$). The main rationale for this is the fact that the micro-perfusion effect, if exists, only appears in the low b-value range. In case that the micro-perfusion effect is apparent, (see ROI_2 in FIG. 4) the DW-MRI signal intensities curve exhibits a significant angle (hereinafter called "knee") which cannot be fitted mono-exponentially (see FIG. 4). This angle is the result of two different phenomena; the micro-perfusion and the true diffusion effect. The mono-exponential model can fail fitting the area where the "knee" appears, thus giving a very low adjusted-$R^2$ value compared to the one from the IVIM model (see Table 1). Conversely, in the true diffusion b-value range (blue box in FIG. 4), the effect of the micro-perfusion is eliminated and both models can accurately fit the DW-MRI data.

On the other hand, in case of examining an area with absence of micro-perfusion, thus absence of the "knee" effect (see indicative ROI_1), the adjusted-$R^2$ only at low b-values are very high and the exemplary methods described herein, such as that in FIG. 1, correctly assigns the mono-exponential model.

Therefore, in one implementation, the right model can be selected for each voxel depending on the adjusted-$R^2$ goodness fit, measured only in the low b-value range (up to 300 s/mm$^2$).

In another implementation, the goodness of fit from the adjusted diffusion analysis models can be implemented using the root-mean-square error (RMSE) instead of the adjusted R-square coefficient ($R^2$). The RMSE parameter is the sample standard deviation of the differences between the observed outcome values, for example, estimated DW-MRI signal intensities at different b-values from the diffusion analysis models, and expected signal intensities at different b-values from the DW-MRI data.

As previously mentioned, AEW provides tools to select appropriate b-values for estimating the perfusion and diffusion effect using the IVIM model. According to the IVIM theory, a voxel or a ROI with a blood flow vasculature area, thus micro-perfusion activity in the low b-value range, shows bi-exponential signal attenuation ("knee" effect), micro-perfusion and true-diffusion decaying form as depicted respectively in FIG. 10. The IVIM DW-MRI bi-exponential signal attenuation as a function of the b-values is composed by adding the mono-exponential decaying form of the true-diffusion and the micro-perfusion, as shown in the following equation (blue and red box respectively). From a mathematical perspective, the higher the perfusion fraction (f) the more the DW-MRI signal attenuation is influenced by the micro perfusion activity.

$$S_b = S_0 * ((1-f)*\exp(-b*D) + f*\exp(-b*D^*))$$

Figure 11:
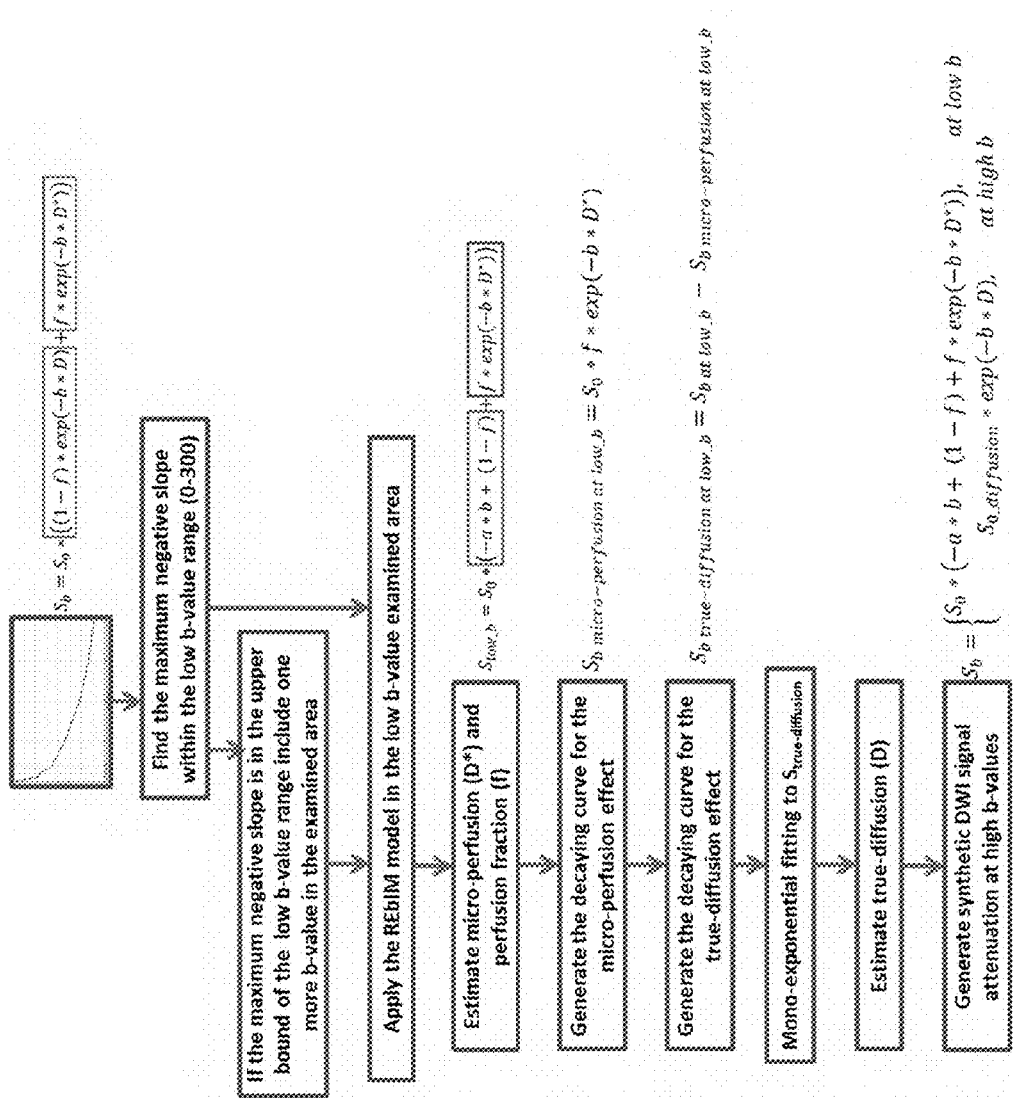
FIG. 11 is an exemplary flowchart of the Reduced b-values Incoherent Motion (REbIM) model, according to an implementation of the present subject matter.
Figure 12:
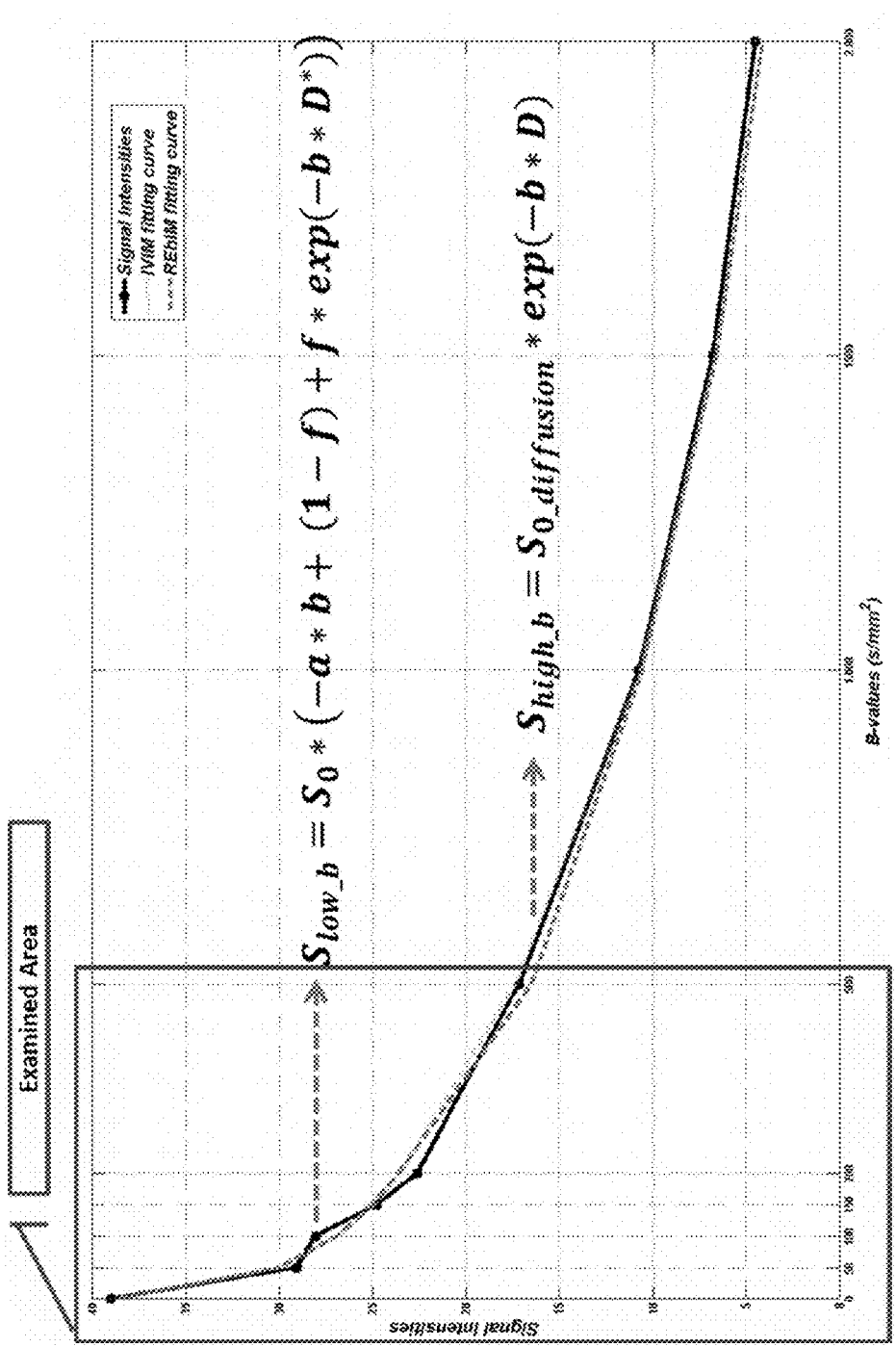
FIG. 12 is a graphical representation of mean value of the signal intensities of ROI_2 (black dotted line) and the mean fitted signal attenuation decaying curve from the IVIM and the exemplary REbIM model (light gray and dark gray curves respectively), according to an implementation of the present subject matter.
Figure 13:
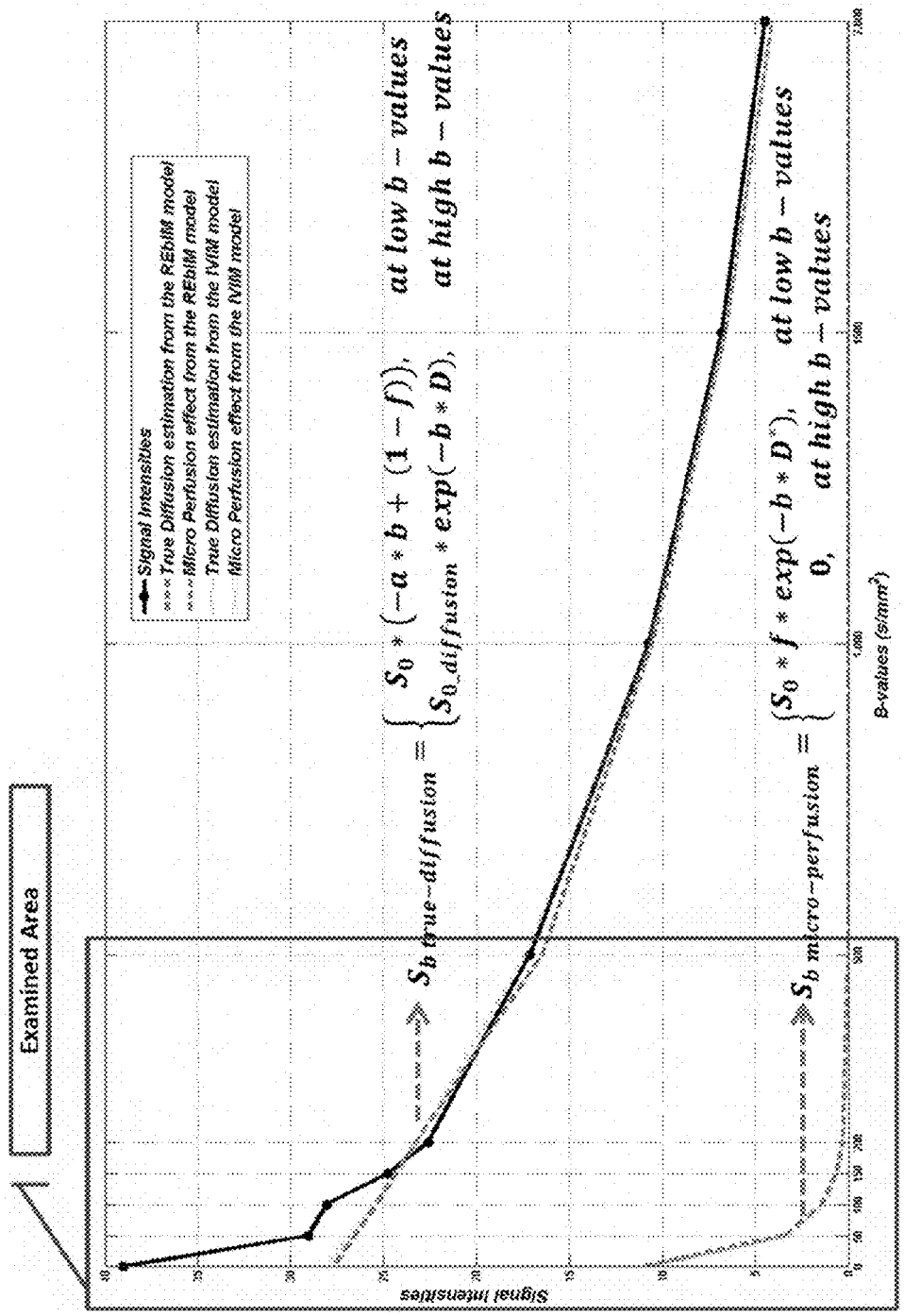
FIG. 13 is a graphical representation of mean value of the signal intensities of ROI_2 (black dotted line) and the estimated mean true-diffusion and micro-perfusion decaying curves from the IVIM and the exemplary REbIM model (light gray and dark gray curves respectively), according to an implementation of the present subject matter.
Figure 14:
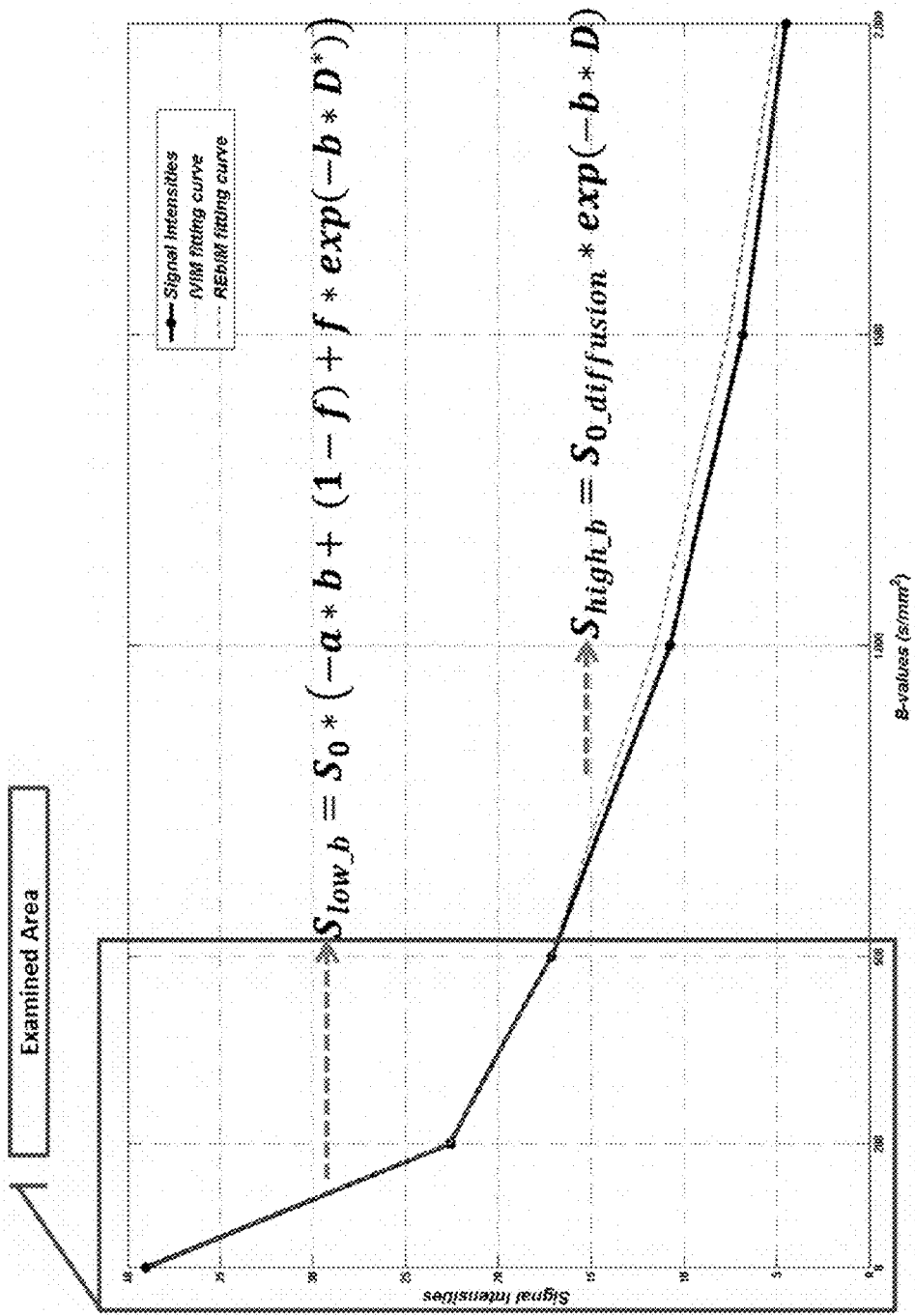
FIG. 14 is a graphical representation of mean value of the signal intensities of ROI_2 (black dotted line) and the mean fitted signal attenuation decaying curve from the IVIM and the exemplary REbIM model (light gray and dark gray curves respectively) using less b-values in the low b-value range, according to an implementation of the present subject matter.
Figure 15:
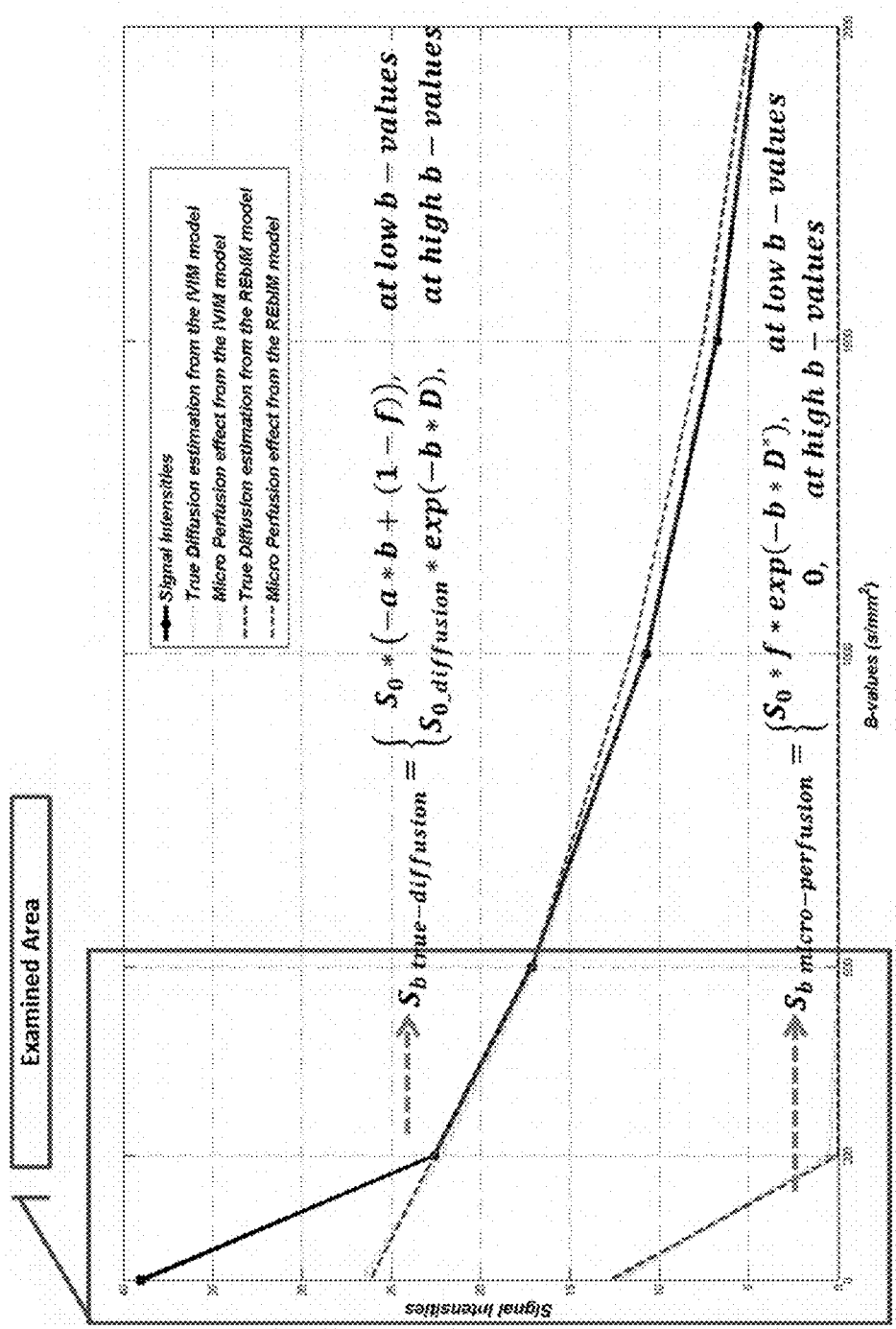
FIG. 15 is a graphical representation of mean value of the signal intensities of ROI_2 (black dotted line) and the estimated mean true-diffusion and micro-perfusion decaying curves from the IVIM and the exemplary REbIM model (light gray and dark gray curves respectively) using less b-values in the low b-value range, according to an implementation of the present subject matter.
Figure 16:
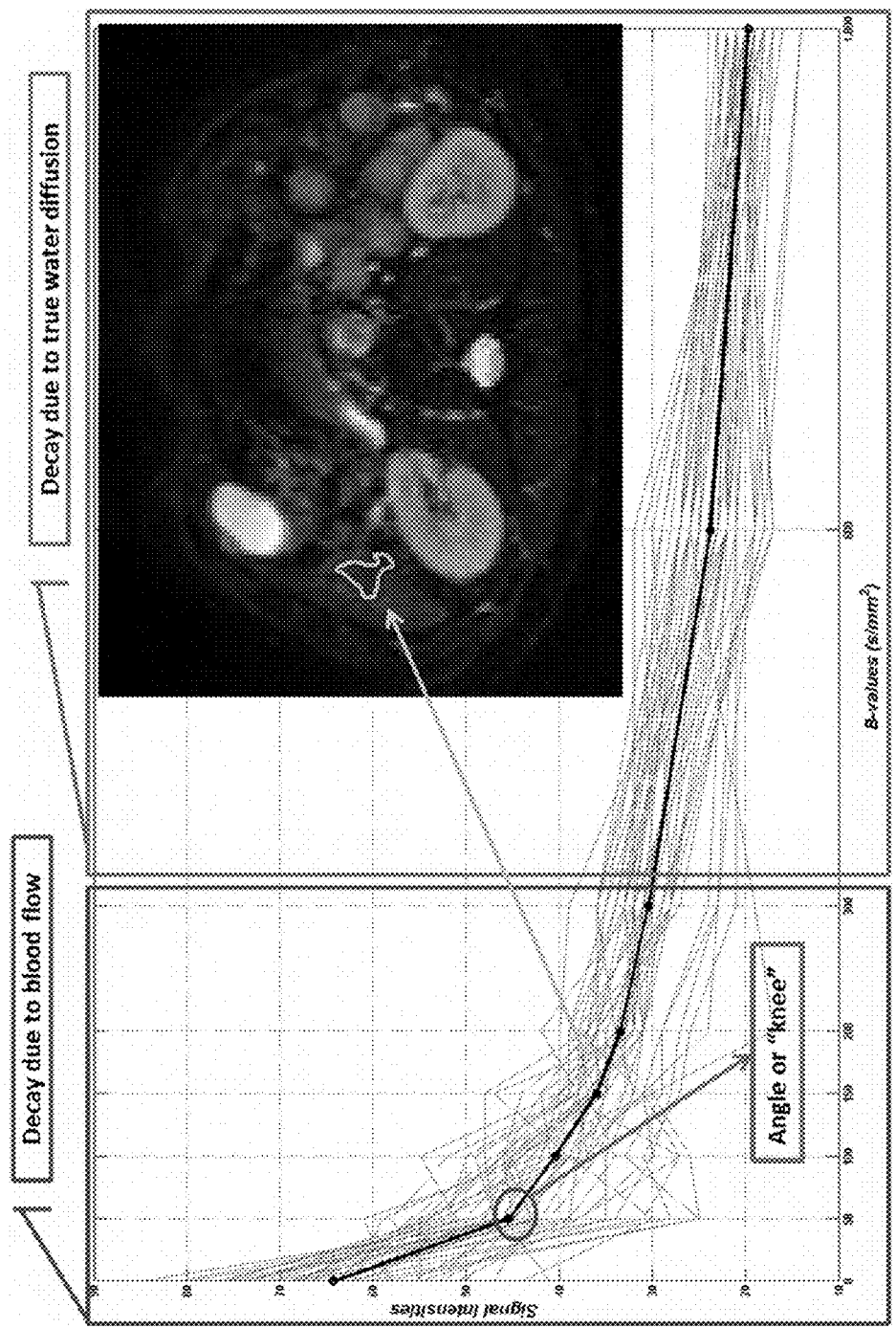
FIG. 16 is a graphical representation of signal attenuation of each voxel of ROI_3 (gray curves) and their mean value (black curves with dots) as a function of b-values 0, 50, 100, 150, 200, 300, 600 and 1000, according to an implementation of the present subject matter.
Figure 17:
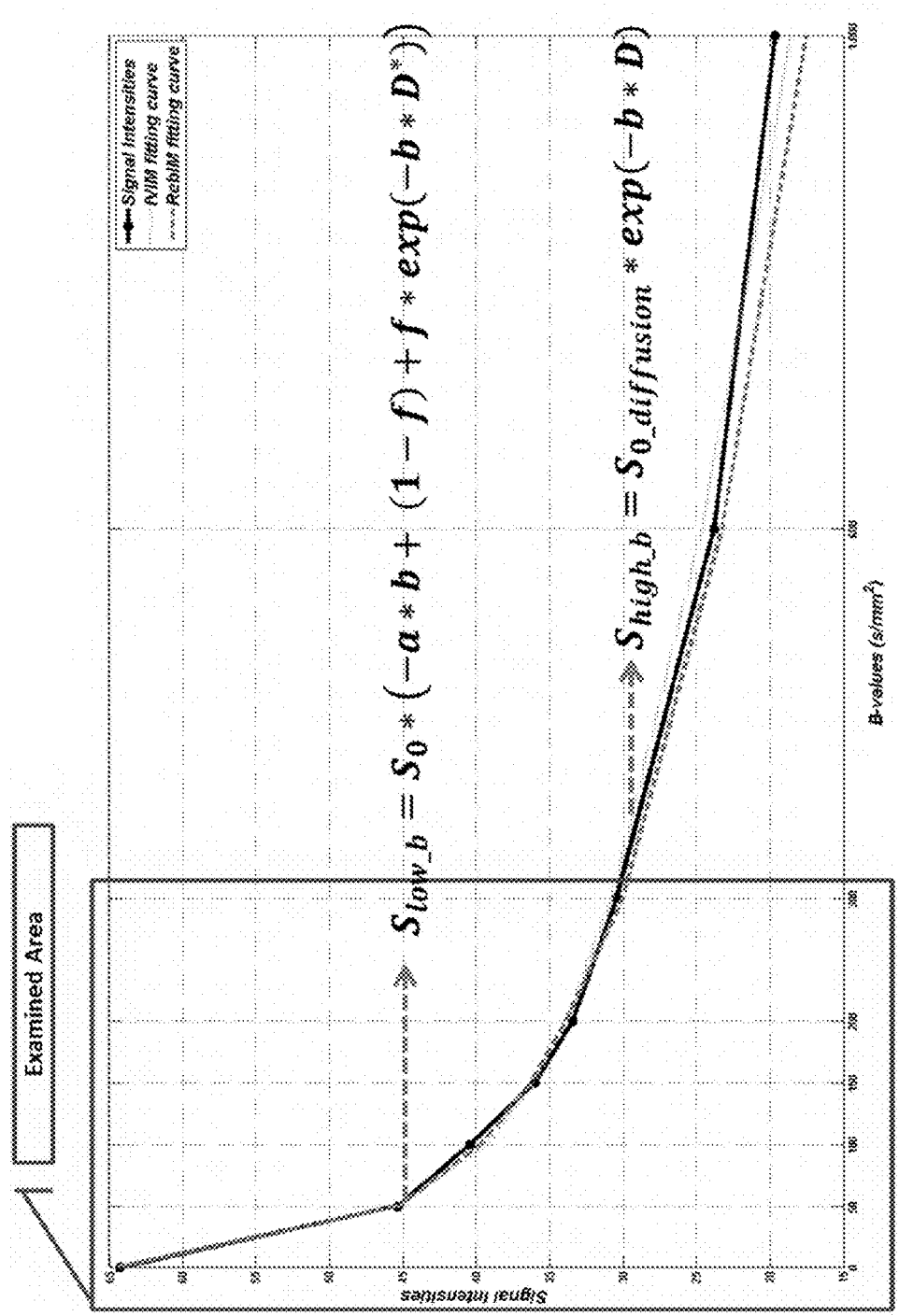
FIG. 17 is a graphical representation of mean value of the signal intensities of ROI_3 (black dotted line) and the mean fitted signal attenuation decaying curve from the IVIM and the exemplary REbIM model (light gray and dark gray curves respectively), according to an implementation of the present subject matter.
Figure 18:
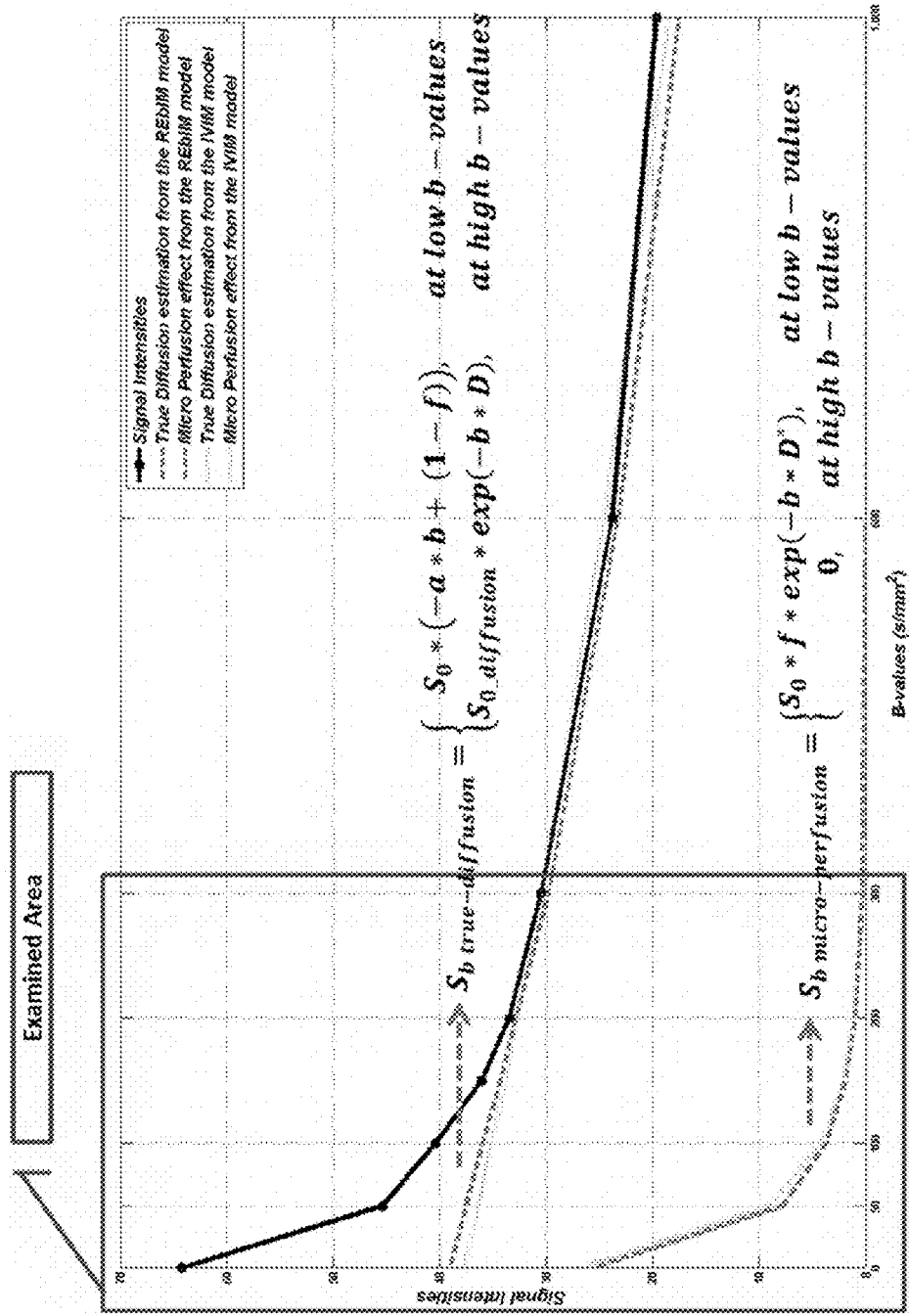
FIG. 18 is a graphical representation of mean value of the signal intensities of ROI_3 (black dotted line) and the estimated mean true-diffusion and micro-perfusion decaying curves from the IVIM and the exemplary REbIM model (light gray and dark gray curves respectively), according to an implementation of the present subject matter.
Figure 19:
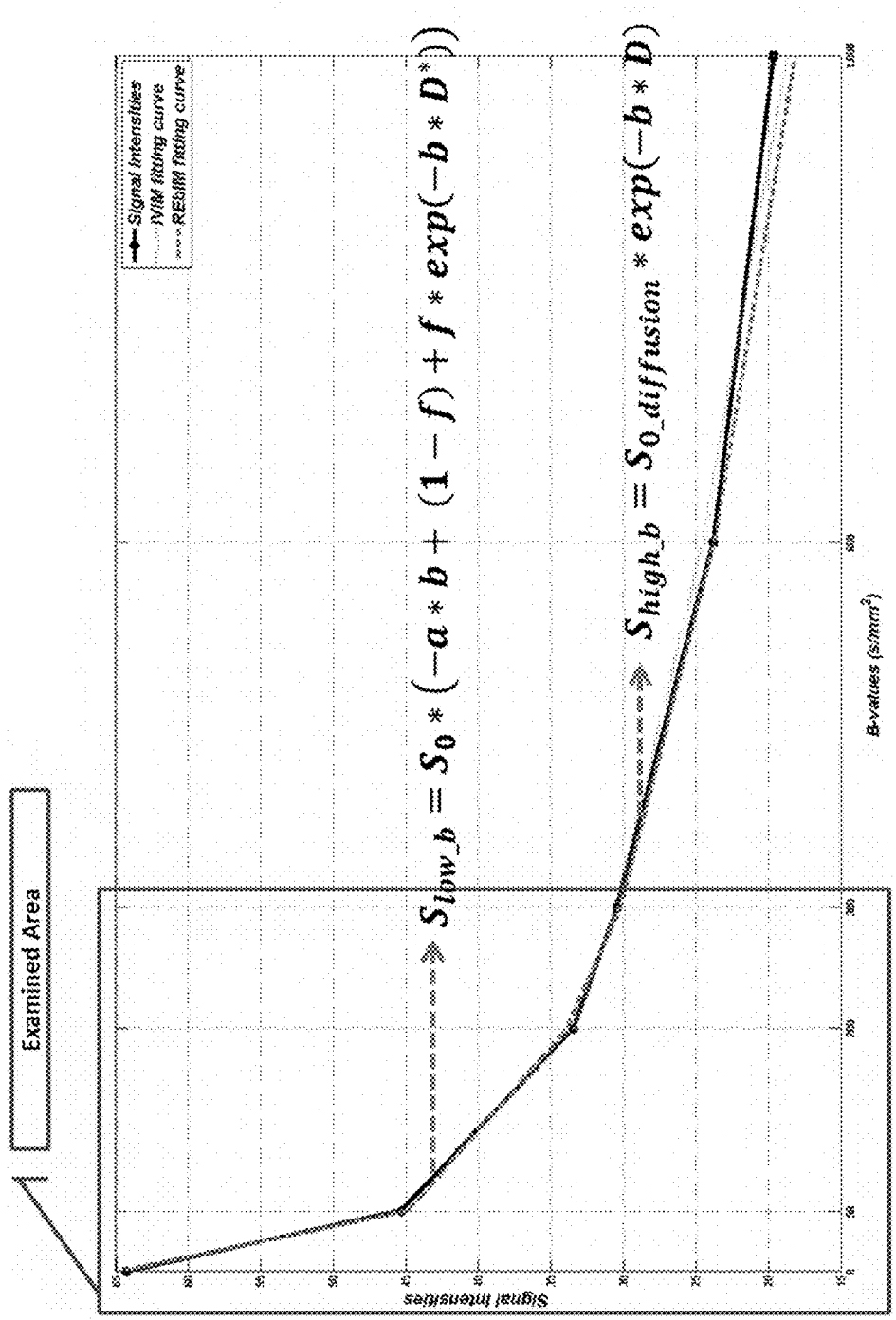
FIG. 19 is a graphical representation of mean value of the signal intensities of ROI_3 (black dotted line) and the mean fitted signal attenuation decaying curve from the IVIM and the exemplary REbIM model (light gray and dark gray curves respectively) using less b-values in the low b-value range, according to an implementation of the present subject matter.
Figure 20:
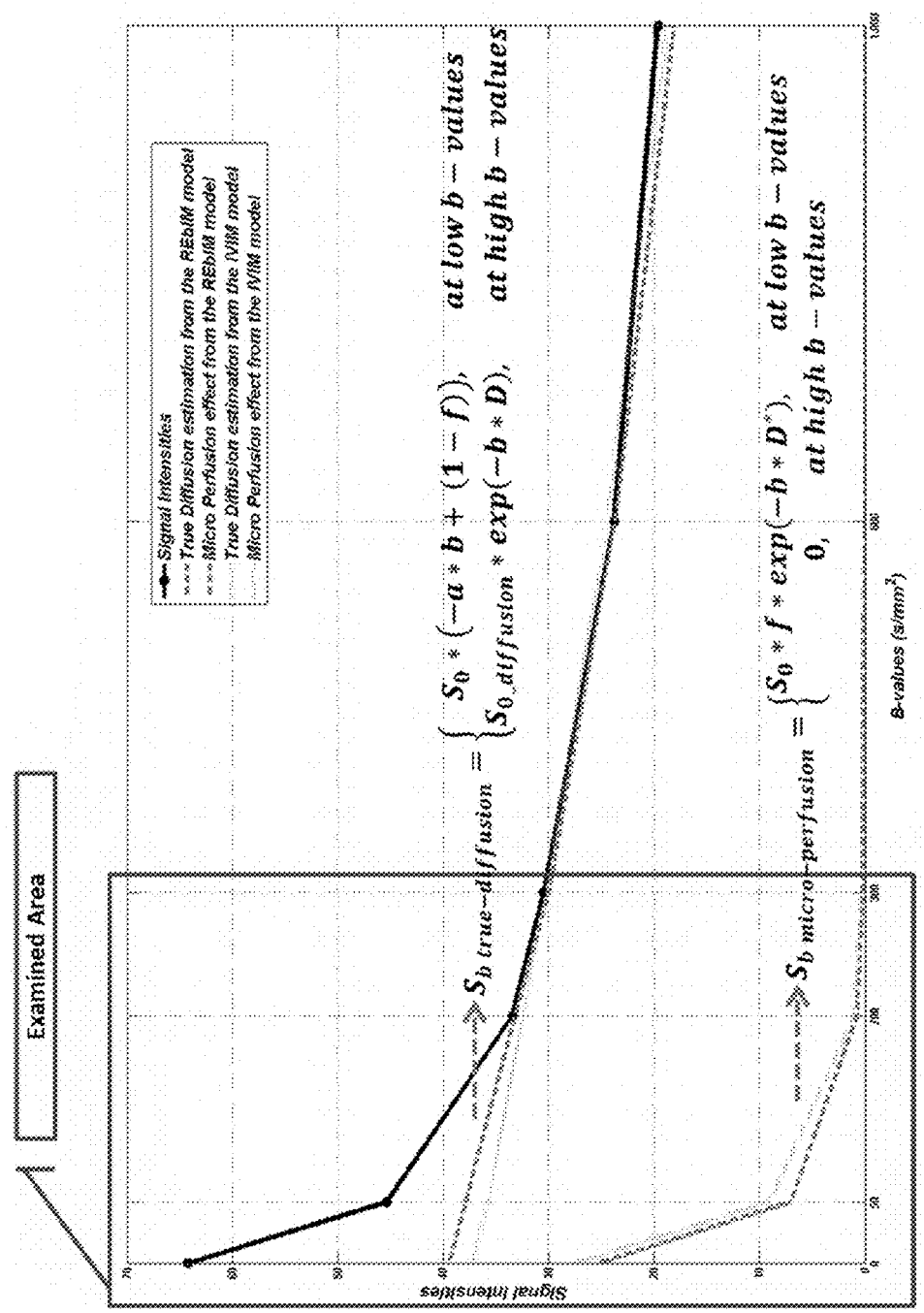
FIG. 20 is a graphical representation of mean value of the signal intensities of ROI_3 (black dotted line) and the estimated mean true-diffusion and micro-perfusion decaying curves from the IVIM and the exemplary REbIM model (light gray and dark gray curves respectively) using less b-values in the low b-value range, according to an implementation of the present subject matter.

According to the literature, the IVIM model requires signal intensities from both the low and the high b-value range in order to measure the micro-perfusion and the true-diffusion activity. In the exemplary REbIM model, it is shown that all the available information is hidden in the low b-value range; therefore no high b-values are required for computing the diffusion parameters. The overall flowchart of the exemplary REbIM model is depicted in FIG. 11. At first, the maximum negative slope of the DWI-MRI signal attenuation of a voxel or a ROI is found within the low b-value range (from 0 to 300 s/mm$^2$) via the derivative of the signal. If the maximum negative slope is the upper bound of the low b-value range, the examined area (see for example FIG. 12, highlighted by a red box) is expanded by one more b.

Figure 10:
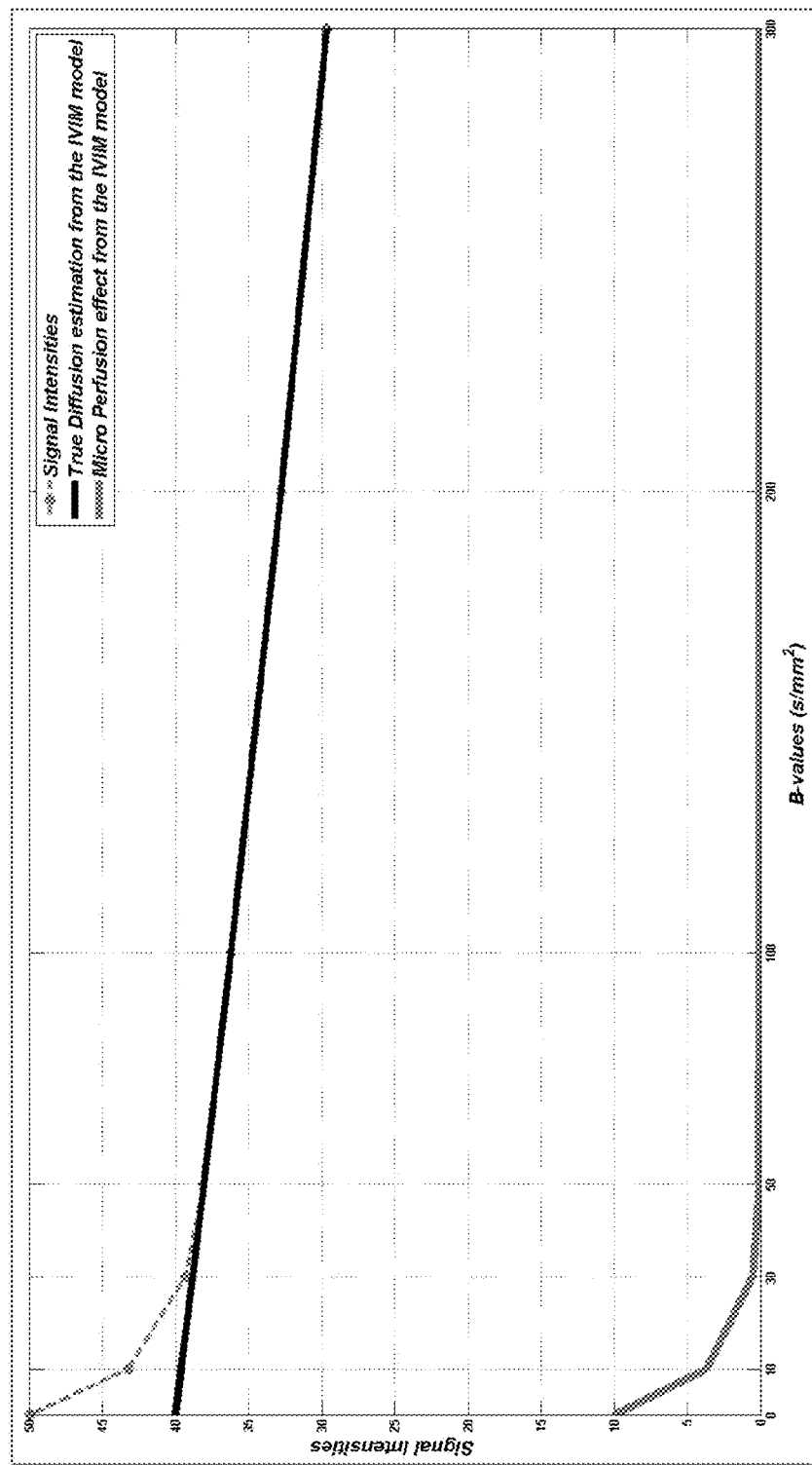
FIG. 10 is a graphical representation of the bi-exponential decaying form of a voxel/ROI in the low b-value range, according to an implementation of the present subject matter.

As seen in FIG. 10, by giving specific values for D, D* and f in the IVIM formula, the micro-perfusion effect shows a fast decay in its signal attenuation as a function of the b-values. On the other hand, true-diffusion shows a much slower process and its exponential decay starts at higher b-values (over 300 s/mm$^2$). In the low b-value range, true diffusion is decaying very smoothly and "meets" the IVIM bi-exponential decaying form in the high b-value range. Due to the slow decay of the true-diffusion signal attenuation we can assume that the second mono-exponential term in the IVIM model which represents true-diffusion (TrueDiffusion=$S_0*(1-f)*\exp(-b*D)$) highlighted by the blue box) can be approximated, in the low b-value range, by a linear function of the form:

$$y = a'*x + c$$

where α' is the slope of the function and c the intercept. Additionally, intercept c can be replaced by the term $S_0*(1-f)$ which is the result of the mono-exponential true-diffusion decaying form when b-value is zero. The slope α' can be replaced by the term $α'=S_0*a$, where $α=S_0/α'$ is the adjusted slope of the true-diffusion signal linear approximation in the low b-values. Therefore, the DW-MRI bi-exponential decaying form of the IVIM model in the low b-value range can be replaced by the following equation:

$$S_{low\_b} = S_0 * (-a*b + (1-f) + f*\exp(-b*D^*))$$

Perfusion fraction (f), micro-perfusion (D*) and the adjusted slope (α) of the linear representation of the true-diffusion at low b-values can be estimated using non-linear least-squares fitting techniques using at least 3 b-values. In one implementation, least-squares techniques are applied to fit a parameterized function to a set of known data points (signal intensities as a function of the b-values in this case) by minimizing the sum of squares of the errors between the data and the function, involving an iterative fitting process for optimizing the parameter values. The non-linearity behavior arises due to the non-linear correlation between the data points and the function. The trust-region-reflective algorithm (see, e.g. Coleman, T. F. and Y. Li, "An Interior, Trust Region Approach for Nonlinear Minimization Subject to Bounds," SIAM Journal on Optimization, Vol. 6, pp. 418-445, 1996) can be used as the curve-fitting method in the applied least-square technique. The signal attenuation $S_{low\_b}$ as a function of the b-values can then be estimated. See the fitting curve from the examined b-value area highlighted by the red box in FIGS. 12, 14, 17, and 19. The signal attenuation of the micro-perfusion effect at the low b-value range is given by the exponential part of the $S_{low\_b}$:

$$S_{b\ micro\text{-}perfusion\ at\ low\_b} = S_0 * f * \exp(-b*D^*)$$

In one implementation, the true-diffusion at the low b-value range is estimated as follows: The DW-MRI signal intensity curve ($S_b$) at the low b-value range is subtracted by the micro-perfusion decaying form, generated by the estimated parameters related to the micro-perfusion effect ($D^*$ and f), as presented by the previous equation. The remaining signal intensity as a function of the b-values reflects the true-diffusion signal.

The signal intensity after the subtraction was fitted linearly where the true-diffusion parameter (D) is estimated.

$$S_{b\ true\text{-}diffusion\ at\ low\_b} = S_0 * (-a*b + (1-f))$$

Summing up, once the fitting process has been completed, the modeled system can generate the signal attenuation decaying form of micro-perfusion and true-diffusion as a function of every b-value according to the following equations:

$$S_{b\ micro\text{-}perfusion} = \begin{cases} S_0 * f * \exp(-b*D^*), & \text{at low } b\text{-values (examined area)} \\ 0, & \text{at high } b\text{-values} \end{cases}$$

$$S_{b\ true\text{-}diffusion} = \begin{cases} S_0 * (-a*b + (1-f)), & \text{at low } b\text{-values (examined area)} \\ S_{0\_diffusion} * \exp(-b*D), & \text{at high } b\text{-values} \end{cases}$$

where $S_{0\_diffusion}$ is the signal intensity of the true-diffusion in the absence of diffusion weighting (b=0). The exemplary REbIM implementation is then following the equation below:

$$S_b = \begin{cases} S_0 * (f * \exp(-b*D^*) - a*b + (1-f)), & \text{at low } b\text{-values} \\ S_{0\_diffusion} * \exp(-b*D), & \text{at high } b\text{-values} \end{cases}$$

The REbIM model can be implemented on real data. For example, in one implementation, two different ROIs were used for the evaluation of the exemplary REbIM model. The first was ROI_2 previously used in the determination of the goodness of fit in the low b-value range. The second, named as ROI_3, was also a region in the liver parenchyma with excluded visible vessels from another examination.

A comparison between the IVIM and the exemplary REbIM model is presented in the following sections. Initially, DWI-MRI signal intensities from ROI_2 and ROI_3 for all the b-values of the examination within the low b-value range were used for the evaluation of the exemplary REbIM model respectively. Due to the MRI protocol of the examination where ROI_2 corresponds, no MRI signal was acquired at b-value=300 s/mm² and the low b-value range of the exemplary method was expanded to 500 s/mm². On the other hand, the low b-value range in case of performing DWI analysis in ROI_3 was from 0 to 300 s/mm². For comparative purposes, each analysis was also performed by the IVIM model adding each time the b-values from the high b-value range. Analytically, the low b-value range for ROI_2 and ROI_3 was:

ROI_2: b-values=0, 50, 100, 150, 200 and 500 s/mm² plus 1000, 1500 and 2000 for the IVIM. Results are presented in Table 3.

TABLE 3

Quantitative representation of the DWI analysis for ROI_2 when applied to the IVIM and exemplary REbIM models

|  | True Diffusion (D) mean value | Micro Perfusion (D*) mean value | Perfusion Fraction (f) mean value | Overall Adjusted $R^2$ mean value | Adjusted $R^2$ low b-value area | Adjusted $R^2$ high b-value area |
|---|---|---|---|---|---|---|
| Exemplary REbIM | 0.9*10⁻³ | 33*10-3 | 30.70% | 98.86% | 97.57% | 97.98% |
| IVIM | 1*10⁻³ | 32*10-3 | 27.69% | 99.29% | 98.57% | 99.97% |

ROI_2: b-values=0, 200 and 500 s/mm² plus 1000, 1500 and 2000 for the IVIM. Results are presented in Table 4.

TABLE 4

Quantitative representation of the DWI analysis for ROI_2 when applied to the IVIM and exemplary REbIM models (less b-values in the low b-value range)

|  | True Diffusion (D) mean value | Micro Perfusion (D*) mean value | Perfusion Fraction (f) mean value | Overall Adjusted $R^2$ mean value | Adjusted $R^2$ low b-value area | Adjusted $R^2$ high b-value area |
|---|---|---|---|---|---|---|
| Exemplary REbIM | 0.9*10⁻³ | 70*10-3 | 32.3% | 99.64% | 100% | 99.01% |
| IVIM | 0.9*10⁻³ | 59*10-3 | 31.9% | 99.87% | 99.77% | 99.92% |

ROI_3: b-values=0, 50, 100, 150, 200 and 300 s/mm² plus 600 and 1000 for the IVIM. Results are presented in Table 5.

TABLE 5

Quantitative representation of the DWI analysis for ROI_3 when applied to the IVIM and exemplary REbIM models

|  | True Diffusion (D) mean value | Micro Perfusion (D*) mean value | Perfusion Fraction (f) mean value | Overall Adjusted R² mean value | Adjusted R² low b-value area | Adjusted R² high b-value area |
| --- | --- | --- | --- | --- | --- | --- |
| Exemplary REbIM | $0.9*10^{-3}$ | $39*10{-3}$ | 38.25% | 95.74% | 99.13% | 92.02% |
| IVIM | $0.7*10^{-3}$ | $30*10{-3}$ | 40.50% | 95.88% | 99.29% | 93.18% |

To further compare the exemplary method with IVIM an analysis has also been performed for ROI_2 and ROI_3 using less b-values from their initial low b-value range respectively. The low b-value ranges were:

ROI_3: b-values=0, 50, 200 and 300 s/mm² plus 600 and 1000 for the IVIM. Results are presented in Table 6.

TABLE 6

Quantitative representation of the DWI analysis for ROI_3 when applied the IVIM and exemplary REbIM models (less b-values in the low b-value range)

|  | True Diffusion (D) mean value | Micro Perfusion (D*) mean value | Perfusion Fraction (f) mean value | Overall Adjusted R² mean value | Adjusted R² low b-value area | Adjusted R² high b-value area |
| --- | --- | --- | --- | --- | --- | --- |
| Exemplary REbIM | $0.9*10^{-3}$ | $37*10{-3}$ | 38.02% | 97.42% | 98.93% | 94.82% |
| IVIM | $0.7*10^{-3}$ | $27*10{-3}$ | 41.46% | 96.22% | 98.39% | 92.58% |

The bi-exponential mean values of the fitting curves, from the IVIM and the exemplary REbIM model, to the DWI-MRI mean signal intensities of ROI_2 and ROI_3 as a function of the b-values are displayed in FIG. 12, FIG. 14, FIG. 17 and FIG. 19 respectively. Accordingly, micro-perfusion and true-diffusion decaying curves from both the IVIM model and the exemplary REbIM model are depicted in FIG. 13, FIG. 15, FIG. 18 and FIG. 20. Finally, a quantitative representation for all the scenarios mentioned above is given in Table 3, Table 4, Table 5 and Table 6.

In every scenario, even in cases where less b-values from the low b-value range were used, the exemplary REbIM implementation fits accurately, and the DWI-MRI signal intensities from both ROIs showed a goodness of fit similar to the IVIM model. Moreover, the micro-perfusion (D*), true-diffusion (D), and perfusion fraction (f) parameters estimation from the exemplary REbIM model have almost the same values with the estimated, by the IVIM, parameters for the micro-perfusion and true-diffusion activity. The exemplary REbIM model implementation has been tested and performed accurately using ROIs from real data that show a bi-exponential behavior in their signal attenuation decaying form, and can be an alternative or complementary model in case a voxel or ROI shows micro-perfusion activity.

In another implementation (see FIG. 22) based on the exemplary RebIM model as outlined in FIG. 11, the model is extended to non-Gaussian diffusion by using the Diffusion Kurtosis Imaging (DKI) equation (Jensen, J. H., J. A. Helpern, A. Ramani, H. Lu and K. Kaczynski. 2005. "Diffusional kurtosis imaging: the quantification of non-Gaussian water diffusion by means of magnetic resonance imaging." Magn Reson Med 53(6):1432-1440.):

$$S_b = S_0 * \exp(-b*D + 1/6*b^2*D^2*K_{app}).$$

where $K_{app}$ is the kurtosis parameter. DKI has been employed to estimate the $K_{app}$ parameter at high b-values (typically not less than 1000 s/mm²) in order to express the degree of non-Gaussian behavior, reflecting the structural changes that occur in tissues due to pathological events. A classification pseudo-colored map can then be generated by the determined kurtosis coefficient $K_{app}$ in every voxel of the ROI using the equation below:

$$\text{Kurtosis Classification} = \begin{cases} 0, & \text{if } K_{app} = 0 \\ 1, & \text{if } 0 < K_{app} < \text{threshold} \\ 2, & \text{if } K_{app} > \text{threshold} \end{cases}$$

In one implementation, a kurtosis classification equal to zero indicates absence of the non-Gaussian diffusion behavior ($K_{app}=0$), whereas a kurtosis coefficient greater than zero but less than a threshold (typically equal to one) indicates low non-Gaussian (low kurtosis). When $K_{app}$ is higher than the threshold, high non-Gaussian (high kurtosis) behavior is assumed. The exemplary method can be used to estimate kurtosis by a) computing D using, for example, only the low b-value range using the exemplary REbIM model according to the workflow depicted in FIG. 11; and b) then using D to compute $K_{app}$ using high b-values (typically >1000 s/mm²) from the DKI equation shown above. Therefore, the exemplary non-Gaussian REbIM model can yield $K_{app}$ parameters with less b-values than traditional approaches. A recent study (Lu, Y., J. F. Jansen, Y. Mazaheri, H. E. Stambuk, J. A. Koutcher and A. Shukla-Dave. 2012. "Extension of the intravoxel incoherent motion model to non-gaussian diffusion in head and neck cancer." J Magn Reson Imaging 36(5):1088-1096.) presented a non-Gaussian model combining the IVIM and the DKI model by giving estimations for the parameters f, D, D* and $K_{app}$. This model however requires a wider range of b-values from low b-values to high (i.e. higher than 1000 s/mm²).

Figure 21:
FIG. 21 is a snapshot of an exemplary computer implemented application for testing, evaluating and comparing the results of the exemplary REbIM model with the conventional approaches, according to an implementation of the present subject matter.
Figure 22:
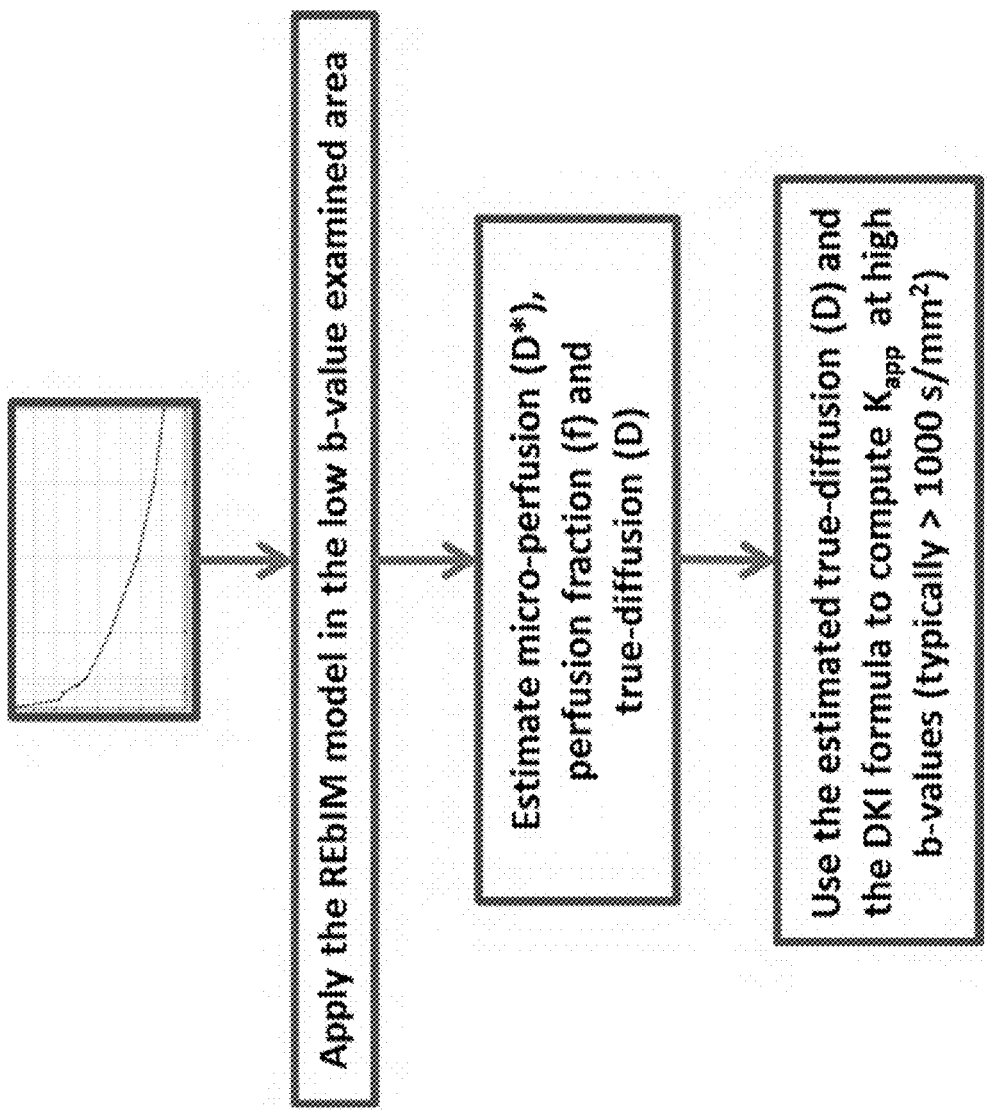
FIG. 22 is a workflow of the exemplary REbIM model, extended to the non-Gaussian diffusion, according to an embodiment of the current subject matter.

The aforementioned implementations can be implemented using software applications, developed in various programming languages, for example, MATLAB. The software can also be equipped with a graphical user interface (GUI), to assist users running diffusion analysis in a userfriendly manner. To this end, FIG. 21 illustrates a snapshot of an exemplary computer implemented application for testing, evaluating and comparing the results of AEW with the conventional approaches, according to an implementation of the present subject matter. FIG. 22 is a workflow of the exemplary REbIM model, extended to the non-Gaussian diffusion.

AEW Controller

Figure 23:
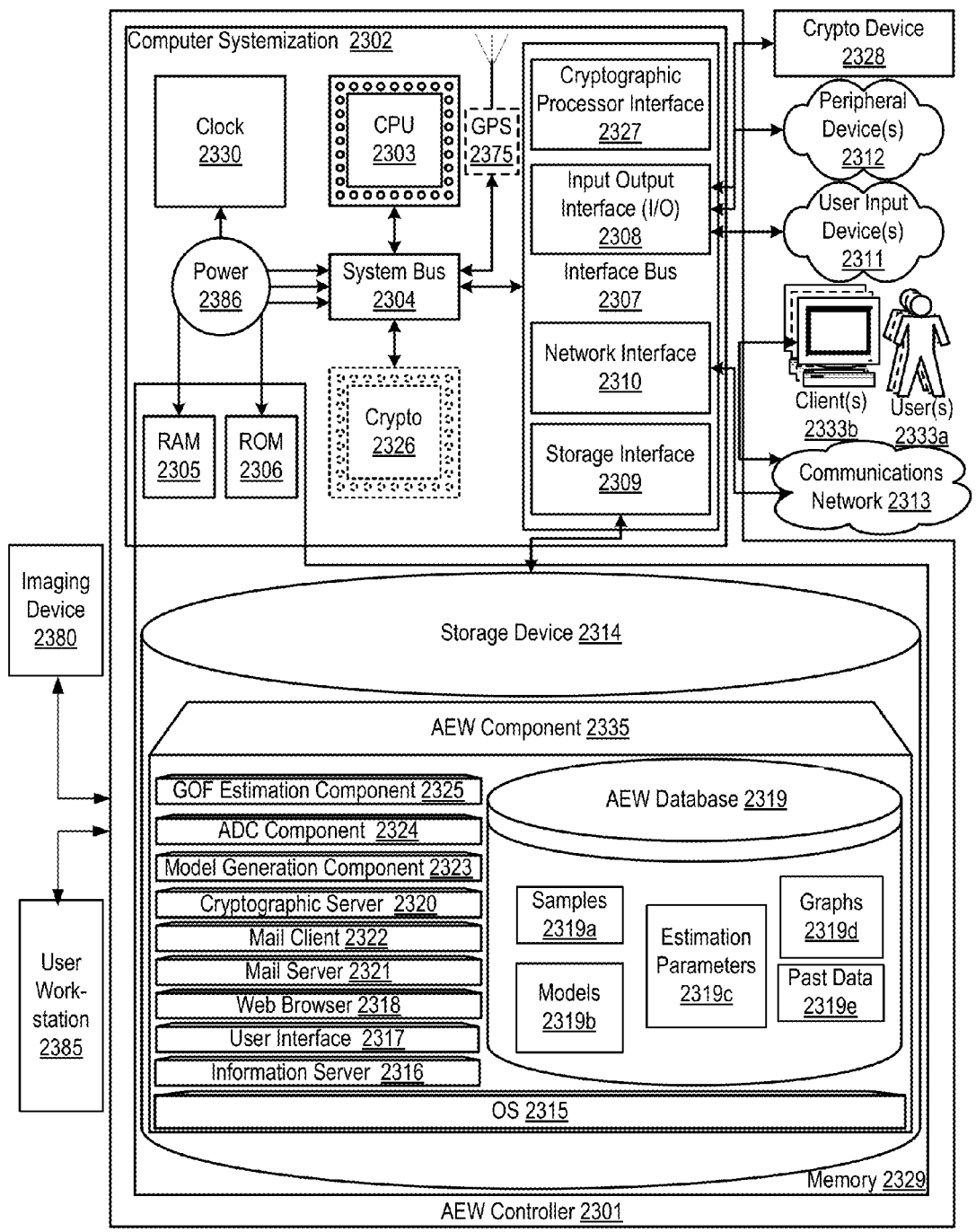
FIG. 23 is a block diagram illustrating embodiments of an AEW controller, according to an embodiment of the present subject matter.

FIG. 23 illustrates inventive aspects of a AEW controller 2301 in a block diagram. In this embodiment, the AEW controller 2301 may serve to aggregate, process, store, search, serve, identify, instruct, generate, match, and/or facilitate interactions with a computer through user-selected information resource collection generation and management technologies, and/or other related data.

Typically, users, which may be people and/or other systems, may engage information technology systems (e.g., computers) to facilitate information processing. In turn, computers employ processors to process information; such processors 2303 may be referred to as central processing units (CPU). One form of processor is referred to as a microprocessor. CPUs use communicative circuits to pass binary encoded signals acting as instructions to enable various operations. These instructions may be operational and/or data instructions containing and/or referencing other instructions and data in various processor accessible and operable areas of memory 2329 (e.g., registers, cache memory, random access memory, etc.). Such communicative instructions may be stored and/or transmitted in batches (e.g., batches of instructions) as programs and/or data components to facilitate desired operations. These stored instruction codes, e.g., programs, may engage the CPU circuit components and other motherboard and/or system components to perform desired operations. One type of program is a computer operating system, which, may be executed by CPU on a computer; the operating system enables and facilitates users to access and operate computer information technology and resources. Some resources that may be employed in information technology systems include: input and output mechanisms through which data may pass into and out of a computer; memory storage into which data may be saved; and processors by which information may be processed. These information technology systems may be used to collect data for later retrieval, analysis, and manipulation, which may be facilitated through a database program. These information technology systems provide interfaces that allow users to access and operate various system components.

In one embodiment, the AEW controller 2301 may be connected to and/or communicate with entities such as, but not limited to: one or more users from user input devices 2311; peripheral devices 2312; an optional cryptographic processor device 2328; and/or a communications network 2313.

Networks are commonly thought to comprise the interconnection and interoperation of clients, servers, and intermediary nodes in a graph topology. It should be noted that the term "server" as used throughout this application refers generally to a computer, other device, program, or combination thereof that processes and responds to the requests of remote users across a communications network. Servers serve their information to requesting "clients." The term "client" as used herein refers generally to a computer, program, other device, user and/or combination thereof that is capable of processing and making requests and obtaining and processing any responses from servers across a communications network. A computer, other device, program, or combination thereof that facilitates, processes information and requests, and/or furthers the passage of information from a source user to a destination user is commonly referred to as a "node." Networks are generally thought to facilitate the transfer of information from source points to destinations. A node specifically tasked with furthering the passage of information from a source to a destination is commonly called a "router." There are many forms of networks such as Local Area Networks (LANs), Pico networks, Wide Area Networks (WANs), Wireless Networks (WLANs), etc. For example, the Internet is generally accepted as being an interconnection of a multitude of networks whereby remote clients and servers may access and interoperate with one another.

The AEW controller 2301 may be based on computer systems that may comprise, but are not limited to, components such as: a computer systemization 2302 connected to memory 2329.

Computer Systemization

A computer systemization 2302 may comprise a clock 2330, central processing unit ("CPU(s)" and/or "processor(s)" (these terms are used interchangeable throughout the subject matter unless noted to the contrary)) 2303, a memory 2329 (e.g., a read only memory (ROM) 2306, a random access memory (RAM) 2305, etc.), and/or an interface bus 2307, and most frequently, although not necessarily, are all interconnected and/or communicating through a system bus 2304 on one or more (mother)board(s) 2302 having conductive and/or otherwise transportive circuit pathways through which instructions (e.g., binary encoded signals) may travel to effect communications, operations, storage, etc. Optionally, the computer systemization may be connected to an internal power source 2386. Optionally, a cryptographic processor 2326 may be connected to the system bus. The system clock typically has a crystal oscillator and generates a base signal through the computer systemization's circuit pathways. The clock is typically coupled to the system bus and various clock multipliers that will increase or decrease the base operating frequency for other components interconnected in the computer systemization. The clock and various components in a computer systemization drive signals embodying information throughout the system. Such transmission and reception of instructions embodying information throughout a computer systemization may be commonly referred to as communications. These communicative instructions may further be transmitted, received, and the cause of return and/or reply communications beyond the instant computer systemization to: communications networks, input devices, other computer systemizations, peripheral devices, and/or the like. Of course, any of the above components may be connected directly to one another, connected to the CPU, and/or organized in numerous variations employed as exemplified by various computer systems.

The CPU comprises at least one high-speed data processor adequate to execute program components for executing user and/or system-generated requests. Often, the processors themselves will incorporate various specialized processing units, such as, but not limited to: integrated system (bus) controllers, memory management control units, floating point units, and even specialized processing sub-units like graphics processing units, digital signal processing units, and/or the like. Additionally, processors may include internal fast access addressable memory, and be capable of mapping and addressing memory 2329 beyond the processor itself; internal memory may include, but is not limited to: fast registers, various levels of cache memory (e.g., level 1, 2, 3, etc.), RAM, etc. The processor may access this memory through the use of a memory address space that is accessible via instruction address, which the processor can construct and decode allowing it to access a circuit path to a specific memory address space having a memory state. The CPU may be a microprocessor such as: AMD's Athlon, Duron and/or Opteron; ARM's application, embedded and secure processors; IBM and/or Motorola's DragonBall and PowerPC; IBM's and Sony's Cell processor; Intel's Celeron, Core (2) Duo, Itanium, Pentium, Xeon, and/or XScale; and/or the like processor(s). The CPU interacts with memory through instruction passing through conductive and/or transportive conduits (e.g., (printed) electronic and/or optic circuits) to execute stored instructions (i.e., program code) according to conventional data processing techniques. Such instruction passing facilitates communication within the AEW controller and beyond through various interfaces. Should processing requirements dictate a greater amount speed and/or capacity, distributed processors (e.g., Distributed AEW), mainframe, multi-core, parallel, and/or supercomputer architectures may similarly be employed. Alternatively, should deployment requirements dictate greater portability, smaller Personal Digital Assistants (PDAs) may be employed.

Depending on the particular implementation, features of the AEW may be achieved by implementing a microcontroller such as CAST's R8051XC2 microcontroller; Intel's MCS 51 (i.e., 8051 microcontroller); and/or the like. Also, to implement certain features of the AEW, some feature implementations may rely on embedded components, such as: Application-Specific Integrated Circuit ("ASIC"), Digital Signal Processing ("DSP"), Field Programmable Gate Array ("FPGA"), and/or the like embedded technology. For example, any of the AEW component collection (distributed or otherwise) and/or features may be implemented via the microprocessor and/or via embedded components; e.g., via ASIC, coprocessor, DSP, FPGA, and/or the like. Alternately, some implementations of the AEW may be implemented with embedded components that are configured and used to achieve a variety of features or signal processing.

Depending on the particular implementation, the embedded components may include software solutions, hardware solutions, and/or some combination of both hardware/software solutions. For example, AEW features discussed herein may be achieved through implementing FPGAs, which are a semiconductor devices containing programmable logic components called "logic blocks", and programmable interconnects, such as the high performance FPGA Virtex series and/or the low cost Spartan series manufactured by Xilinx. Logic blocks and interconnects can be programmed by the customer or designer, after the FPGA is manufactured, to implement any of the AEW features. A hierarchy of programmable interconnects allow logic blocks to be interconnected as needed by the AEW system designer/administrator, somewhat like a one-chip programmable breadboard. An FPGA's logic blocks can be programmed to perform the function of basic logic gates such as AND, and XOR, or more complex combinational functions such as decoders or simple mathematical functions. In most FPGAs, the logic blocks also include memory elements, which may be simple flip-flops or more complete blocks of memory. In some circumstances, the AEW may be developed on regular FPGAs and then migrated into a fixed version that more resembles ASIC implementations. Alternate or coordinating implementations may migrate AEW controller features to a final ASIC instead of or in addition to FPGAs. Depending on the implementation all of the aforementioned embedded components and microprocessors may be considered the "CPU" and/or "processor" for the AEW.

Power Source

The power source 2386 may be of any standard form for powering small electronic circuit board devices such as the following power cells: alkaline, lithium hydride, lithium ion, lithium polymer, nickel cadmium, solar cells, and/or the like. Other types of AC or DC power sources may be used as well. In the case of solar cells, in one embodiment, the case provides an aperture through which the solar cell may capture photonic energy. The power cell 2386 is connected to at least one of the interconnected subsequent components of the AEW thereby providing an electric current to all subsequent components. In one example, the power source 2386 is connected to the system bus component 2304. In an alternative embodiment, an outside power source 2386 is provided through a connection across the I/O 2308 interface. For example, a USB and/or IEEE 1394 connection carries both data and power across the connection and is therefore a suitable source of power.

Interface Adapters

Interface bus(ses) 2307 may accept, connect, and/or communicate to a number of interface adapters, conventionally although not necessarily in the form of adapter cards, such as but not limited to: input output interfaces (I/O) 2308, storage interfaces 2309, network interfaces 2310, and/or the like. Optionally, cryptographic processor interfaces 2327 similarly may be connected to the interface bus. The interface bus provides for the communications of interface adapters with one another as well as with other components of the computer systemization. Interface adapters are adapted for a compatible interface bus. Interface adapters conventionally connect to the interface bus via a slot architecture. Conventional slot architectures may be employed, such as, but not limited to: Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and/or the like.

Storage interfaces 2309 may accept, communicate, and/or connect to a number of storage devices such as, but not limited to: storage devices 2314, removable disc devices, and/or the like. Storage interfaces may employ connection protocols such as, but not limited to: (Ultra) (Serial) Advanced Technology Attachment (Packet Interface) ((Ultra) (Serial) ATA(PI)), (Enhanced) Integrated Drive Electronics ((E)IDE), Institute of Electrical and Electronics Engineers (IEEE) 1394, fiber channel, Small Computer Systems Interface (SCSI), Universal Serial Bus (USB), and/or the like.

Network interfaces 2310 may accept, communicate, and/or connect to a communications network 2313. Through a communications network 2313, the AEW controller is accessible through remote clients 2333*b* (e.g., computers with web browsers) by users 2333*a*. Network interfaces may employ connection protocols such as, but not limited to: direct connect, Ethernet (thick, thin, twisted pair 10/100/1000 Base T, and/or the like), Token Ring, wireless connection such as IEEE 802.11a-x, and/or the like. Should processing requirements dictate a greater amount speed and/or capacity, distributed network controllers (e.g., Distributed AEW), architectures may similarly be employed to pool, load balance, and/or otherwise increase the communicative bandwidth required by the AEW controller 2301. A communications network may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like. A network interface may be regarded as a specialized form of an input output interface. Further, multiple network interfaces 2310 may be used to engage with various communications network types 2313. For example, multiple network interfaces may be employed to allow for the communication over broadcast, multicast, and/or unicast networks.

Input Output interfaces (I/O) 2308 may accept, communicate, and/or connect to user input devices 2311, peripheral devices 2312, cryptographic processor devices 2328, and/or the like. I/O may employ connection protocols such as, but not limited to: audio: analog, digital, monaural, RCA, stereo, and/or the like; data: Apple Desktop Bus (ADB), IEEE 1394a-b, serial, universal serial bus (USB); infrared; joystick; keyboard; midi; optical; PC AT; PS/2; parallel; radio; video interface: Apple Desktop Connector (ADC), BNC, coaxial, component, composite, digital, Digital Visual Interface (DVI), high-definition multimedia interface (HDMI), RCA, RF antennae, S-Video, VGA, and/or the like; wireless: 802.11a/b/g/n/x, Bluetooth, code division multiple access (CDMA), global system for mobile communications (GSM), WiMax, etc.; and/or the like. One typical output device may include a video display, which typically comprises a Cathode Ray Tube (CRT) or Liquid Crystal Display (LCD) based monitor with an interface (e.g., DVI circuitry and cable) that accepts signals from a video interface, may be used. The video interface composites information generated by a computer systemization and generates video signals based on the composited information in a video memory frame. Another output device is a television set, which accepts signals from a video interface. Typically, the video interface provides the composited video information through a video connection interface that accepts a video display interface (e.g., an RCA composite video connector accepting an RCA composite video cable; a DVI connector accepting a DVI display cable, etc.).

User input devices 2311 may be card readers, dongles, finger print readers, gloves, graphics tablets, joysticks, keyboards, mouse (mice), remote controls, retina readers, trackballs, trackpads, and/or the like.

Peripheral devices 2312 may be connected and/or communicate to I/O and/or other facilities of the like such as network interfaces, storage interfaces, and/or the like. Peripheral devices may be audio devices, cameras, dongles (e.g., for copy protection, ensuring secure transactions with a digital signature, and/or the like), external processors (for added functionality), goggles, microphones, monitors, network interfaces, printers, scanners, storage devices, video devices, video sources, visors, and/or the like.

It should be noted that although user input devices and peripheral devices may be employed, the AEW controller 2301 may be embodied as an embedded, dedicated, and/or monitor-less (i.e., headless) device, wherein access would be provided over a network interface connection.

Cryptographic units such as, but not limited to, microcontrollers, processors 2326, interfaces 2327, and/or devices 2328 may be attached, and/or communicate with the AEW controller. A MC68HC16 microcontroller, manufactured by Motorola Inc., may be used for and/or within cryptographic units. The MC68HC16 microcontroller utilizes a 16-bit multiply-and-accumulate instruction in the 16 MHz configuration and requires less than one second to perform a 512-bit RSA private key operation. Cryptographic units support the authentication of communications from interacting agents, as well as allowing for anonymous transactions. Cryptographic units may also be configured as part of CPU. Equivalent microcontrollers and/or processors may also be used. Other commercially available specialized cryptographic processors include: the Broadcom's CryptoNetX and other Security Processors; nCipher's nShield, SafeNet's Luna PCI (e.g., 7100) series; Semaphore Communications' 40 MHz Roadrunner 184; Sun's Cryptographic Accelerators (e.g., Accelerator 6000 PCIe Board, Accelerator 500 Daughtercard); Via Nano Processor (e.g., L2100, L2200, U2400) line, which is capable of performing 500+ MB/s of cryptographic instructions; VLSI Technology's 33 MHz 6868; and/or the like.

Memory

Generally, any mechanization and/or embodiment allowing a processor to affect the storage and/or retrieval of information is regarded as memory 2329. However, memory is a fungible technology and resource, thus, any number of memory embodiments may be employed in lieu of or in concert with one another. It is to be understood that the AEW controller and/or a computer systemization may employ various forms of memory 2329. For example, a computer systemization may be configured wherein the functionality of on-chip CPU memory (e.g., registers), RAM, ROM, and any other storage devices are provided by a paper punch tape or paper punch card mechanism; of course such an embodiment would result in an extremely slow rate of operation. In a typical configuration, memory 2329 will include ROM 2306, RAM and a storage device 2314. A storage device 2314 may be any conventional computer system storage. Storage devices may include a drum; a (fixed and/or removable) magnetic disk drive; a magneto-optical drive; an optical drive (i.e., Blueray, CD ROM/RAM/Recordable (R)/ReWritable (RW), DVD R/RW, HD DVD R/RW etc.); an array of devices (e.g., Redundant Array of Independent Disks (RAID)); solid state memory devices (USB memory, solid state drives (SSD), etc.); other processor-readable storage mediums; and/or other devices of the like. Thus, a computer systemization generally requires and makes use of memory.

Component Collection

The memory 2329 may contain a collection of program and/or database components and/or data such as, but not limited to: operating system component(s) 2315 (operating system); information server component(s) 2316 (information server); user interface component(s) 2317 (user interface); Web browser component(s) 2318 (Web browser); database(s) 2319; mail server component(s) 2321; mail client component(s) 2322; cryptographic server component(s) 2320 (cryptographic server); model generation component 2323; comparison component 2324; estimation component 2325; other components (not shown), and/or the like (i.e., collectively a component collection). These components may be stored and accessed from the storage devices and/or from storage devices accessible through an interface bus. Although non-conventional program components such as those in the component collection, typically, are stored in a local storage device 2314, they may also be loaded and/or stored in memory such as: peripheral devices, RAM, remote storage facilities through a communications network, ROM, various forms of memory, and/or the like.

It is to be understood that the present technology may be implemented in various forms of hardware, software, firmware, special purpose processors, or a combination thereof. In one implementation, the methods described herein may be implemented as computer readable program code tangibly embodied in computer-usable media. Computer-usable media may include random access memory (RAM), read only memory (ROM), magnetic floppy disk, flash memory, and other types of memories, or a combination thereof. The computer-readable program code may be executed by CPU 2303 to process images (e.g., MR or CT images) from imaging device 2380 (e.g., MRI or CT scanner). As such, the controller 2301 is a general-purpose computer system that becomes a specific purpose computer system when executing the computer readable program code. The computer readable program code is not intended to be limited to any particular programming language and implementation thereof. It will be appreciated that a variety of programming languages and coding thereof may be used to implement the teachings of the subject matter contained herein.

The controller 2301 may also include an operating system and microinstruction code. The various techniques described herein may be implemented either as part of the microinstruction code or as part of an application program or software product, or combination thereof, which is executed via the operating system. Various other peripheral devices, such as additional data storage devices and printing devices, may be connected to the controller 2301.

The radiologist workstation 2385 may include a computer and appropriate peripherals, such as a keyboard and display, and can be operated in conjunction with the controller 2301. For example, the radiologist workstation 2385 may communicate with the imaging device 2380 so that the image data collected by the imaging device can be rendered at the radiologist workstation 2385 and viewed on the display. Further, the radiologist workstation 2385 may communicate directly with the controller 2301 to access previously processed image data, such as data which has undergone processing by the framework described herein, so that a radiologist can manually verify the results of the framework.

Operating System

The operating system component 2315 is an executable program component facilitating the operation of the AEW controller. Typically, the operating system facilitates access of I/O, network interfaces, peripheral devices, storage devices, and/or the like. The operating system may be a highly fault tolerant, scalable, and secure system such as: Apple Macintosh OS X (Server); AT&T Plan 9; Be OS; Unix and Unix-like system distributions (such as AT&T's UNIX; Berkley Software Distribution (BSD) variations such as FreeBSD, NetBSD, OpenBSD, and/or the like; Linux distributions such as Red Hat, Ubuntu, and/or the like); and/or the like operating systems. However, more limited and/or less secure operating systems also may be employed such as Apple Macintosh OS, IBM OS/2, Microsoft DOS, Microsoft Windows 2000/2003/3.1/95/98/CE/Millenium/NT/Vista/XP (Server), Palm OS, and/or the like. An operating system may communicate to and/or with other components in a component collection, including itself, and/or the like. Most frequently, the operating system communicates with other program components, user interfaces, and/or the like. For example, the operating system may contain, communicate, generate, obtain, and/or provide program component, system, user, and/or data communications, requests, and/or responses. The operating system, once executed by the CPU, may enable the interaction with communications networks, data, I/O, peripheral devices, program components, memory, user input devices, and/or the like. The operating system may provide communications protocols that allow the AEW controller to communicate with other entities through a communications network 2313. Various communication protocols may be used by the AEW controller as a subcarrier transport mechanism for interaction, such as, but not limited to: multicast, TCP/IP, UDP, unicast, and/or the like.

Information Server

An information server component 2316 is a stored program component that is executed by a CPU. The information server may be a conventional Internet information server such as, but not limited to Apache Software Foundation's Apache, Microsoft's Internet Information Server, and/or the like. The information server may allow for the execution of program components through facilities such as Active Server Page (ASP), ActiveX, (ANSI) (Objective-) C (++), C# and/or .NET, Common Gateway Interface (CGI) scripts, dynamic (D) hypertext markup language (HTML), FLASH, Java, JavaScript, Practical Extraction Report Language (PERL), Hypertext Pre-Processor (PHP), pipes, Python, wireless application protocol (WAP), WebObjects, and/or the like. The information server may support secure communications protocols such as, but not limited to, File Transfer Protocol (FTP); HyperText Transfer Protocol (HTTP); Secure Hypertext Transfer Protocol (HTTPS), Secure Socket Layer (SSL), messaging protocols (e.g., America Online (AOL) Instant Messenger (AIM), Application Exchange (APEX), ICQ, Internet Relay Chat (IRC), Microsoft Network (MSN) Messenger Service, Presence and Instant Messaging Protocol (PRIM), Internet Engineering Task Force's (IETF's) Session Initiation Protocol (SIP), SIP for Instant Messaging and Presence Leveraging Extensions (SIMPLE), open XML-based Extensible Messaging and Presence Protocol (XMPP) (i.e., Jabber or Open Mobile Alliance's (OMA's) Instant Messaging and Presence Service (IMPS)), Yahoo! Instant Messenger Service, and/or the like. The information server provides results in the form of Web pages to Web browsers, and allows for the manipulated generation of the Web pages through interaction with other program components. After a Domain Name System (DNS) resolution portion of an HTTP request is resolved to a particular information server, the information server resolves requests for information at specified locations on the AEW controller based on the remainder of the HTTP request. For example, a request such as http://123.124.125.126/myInformation.html might have the IP portion of the request "123.124.125.126" resolved by a DNS server to an information server at that IP address; that information server might in turn further parse the http request for the "/myInformation.html" portion of the request and resolve it to a location in memory containing the information "myInformation.html." Additionally, other information serving protocols may be employed across various ports, e.g., FTP communications across port 21, and/or the like. An information server may communicate to and/or with other components in a component collection, including itself, and/or facilities of the like. Most frequently, the information server communicates with the AEW database 2319, operating systems, other program components, user interfaces, Web browsers, and/or the like.

Access to the AEW database may be achieved through a number of database bridge mechanisms such as through scripting languages as enumerated below (e.g., CGI) and through inter-application communication channels as enumerated below (e.g., CORBA, WebObjects, etc.). Any data requests through a Web browser are parsed through the bridge mechanism into appropriate grammars as required by the AEW. In one embodiment, the information server would provide a Web form accessible by a Web browser. Entries made into supplied fields in the Web form are tagged as having been entered into the particular fields, and parsed as such. The entered terms are then passed along with the field tags, which act to instruct the parser to generate queries directed to appropriate tables and/or fields. In one embodiment, the parser may generate queries in standard SQL by instantiating a search string with the proper join/select commands based on the tagged text entries, wherein the resulting command is provided over the bridge mechanism to the AEW as a query. Upon generating query results from the query, the results are passed over the bridge mechanism, and may be parsed for formatting and generation of a new results Web page by the bridge mechanism. Such a new results Web page is then provided to the information server, which may supply it to the requesting Web browser.

Also, an information server may contain, communicate, generate, obtain, and/or provide program component, system, user, and/or data communications, requests, and/or responses.

User Interface

The function of computer interfaces in some respects is similar to automobile operation interfaces. Automobile operation interface elements such as steering wheels, gearshifts, and speedometers facilitate the access, operation, and display of automobile resources, functionality, and status. Computer interaction interface elements such as check boxes, cursors, menus, scrollers, and windows (collectively and commonly referred to as widgets) similarly facilitate the access, operation, and display of data and computer hardware and operating system resources, functionality, and status. Operation interfaces are commonly called user interfaces. Graphical user interfaces (GUIs) such as the Apple Macintosh Operating System's Aqua, IBM's OS/2, Microsoft's Windows 2000/2003/3.1/95/98/CE/Millenium/NT// XP/Vista/7 (i.e., Aero), Unix's X-Windows (e.g., which may include additional Unix graphic interface libraries and layers such as K Desktop Environment (KDE), mythTV and GNU Network Object Model Environment (GNOME)), web interface libraries (e.g., ActiveX, AJAX, (D)HTML, FLASH, Java, JavaScript, etc. interface libraries such as, but not limited to, Dojo, jQuery(UI), MooTools, Prototype, script.aculo.us, SWFObject, Yahoo! User Interface, any of which may be used and) provide a baseline and means of accessing and displaying information graphically to users.

A user interface component 2317 is a stored program component that is executed by a CPU. The user interface may be a conventional graphic user interface as provided by, with, and/or atop operating systems and/or operating environments such as already discussed. The user interface may allow for the display, execution, interaction, manipulation, and/or operation of program components and/or system facilities through textual and/or graphical facilities. The user interface provides a facility through which users may affect, interact, and/or operate a computer system. A user interface may communicate to and/or with other components in a component collection, including itself, and/or facilities of the like. Most frequently, the user interface communicates with operating systems, other program components, and/or the like. The user interface may contain, communicate, generate, obtain, and/or provide program component, system, user, and/or data communications, requests, and/or responses.

Web Browser

A Web browser component 2318 is a stored program component that is executed by a CPU. The Web browser may be a conventional hypertext viewing application such as Microsoft Internet Explorer or Netscape Navigator. Secure Web browsing may be supplied with 128 bit (or greater) encryption by way of HTTPS, SSL, and/or the like. Web browsers allowing for the execution of program components through facilities such as ActiveX, AJAX, (D)HTML, FLASH, Java, JavaScript, web browser plug-in APIs (e.g., FireFox, Safari Plug-in, and/or the like APIs), and/or the like. Web browsers and like information access tools may be integrated into PDAs, cellular telephones, and/or other mobile devices. A Web browser may communicate to and/or with other components in a component collection, including itself, and/or facilities of the like. Most frequently, the Web browser communicates with information servers, operating systems, integrated program components (e.g., plug-ins), and/or the like; e.g., it may contain, communicate, generate, obtain, and/or provide program component, system, user, and/or data communications, requests, and/or responses. Of course, in place of a Web browser and information server, a combined application may be developed to perform similar functions of both. The combined application would similarly affect the obtaining and the provision of information to users, user agents, and/or the like from the AEW enabled nodes. The combined application may be nugatory on systems employing standard Web browsers.

Mail Server

A mail server component 2321 is a stored program component that is executed by a CPU 2303. The mail server may be a conventional Internet mail server such as, but not limited to sendmail, Microsoft Exchange, and/or the like. The mail server may allow for the execution of program components through facilities such as ASP, ActiveX, (ANSI) (Objective-) C (++), C# and/or .NET, CGI scripts, Java, JavaScript, PERL, PHP, pipes, Python, WebObjects, and/or the like. The mail server may support communications protocols such as, but not limited to: Internet message access protocol (IMAP), Messaging Application Programming Interface (MAPI)/Microsoft Exchange, post office protocol (POP3), simple mail transfer protocol (SMTP), and/or the like. The mail server can route, forward, and process incoming and outgoing mail messages that have been sent, relayed and/or otherwise traversing through and/or to the AEW.

Access to the AEW mail may be achieved through a number of APIs offered by the individual Web server components and/or the operating system.

Also, a mail server may contain, communicate, generate, obtain, and/or provide program component, system, user, and/or data communications, requests, information, and/or responses.

Mail Client

A mail client component 2322 is a stored program component that is executed by a CPU 2303. The mail client may be a conventional mail viewing application such as Apple Mail, Microsoft Entourage, Microsoft Outlook, Microsoft Outlook Express, Mozilla, Thunderbird, and/or the like. Mail clients may support a number of transfer protocols, such as: IMAP, Microsoft Exchange, POP3, SMTP, and/or the like. A mail client may communicate to and/or with other components in a component collection, including itself, and/or facilities of the like. Most frequently, the mail client communicates with mail servers, operating systems, other mail clients, and/or the like; e.g., it may contain, communicate, generate, obtain, and/or provide program component, system, user, and/or data communications, requests, information, and/or responses. Generally, the mail client provides a facility to compose and transmit electronic mail messages.

Cryptographic Server

A cryptographic server component 2320 is a stored program component that is executed by a CPU 2303, cryptographic processor 2326, cryptographic processor interface 2327, cryptographic processor device 2328, and/or the like. Cryptographic processor interfaces will allow for expedition of encryption and/or decryption requests by the cryptographic component; however, the cryptographic component, alternatively, may run on a conventional CPU. The cryptographic component allows for the encryption and/or decryption of provided data. The cryptographic component allows for both symmetric and asymmetric (e.g., Pretty Good Protection (PGP)) encryption and/or decryption. The cryptographic component may employ cryptographic techniques such as, but not limited to: digital certificates (e.g., X.509 authentication framework), digital signatures, dual signatures, enveloping, password access protection, public key management, and/or the like. The cryptographic component will facilitate numerous (encryption and/or decryption) security protocols such as, but not limited to: checksum, Data Encryption Standard (DES), Elliptical Curve Encryption (ECC), International Data Encryption Algorithm (IDEA), Message Digest 5 (MD5, which is a one way hash function), passwords, Rivest Cipher (RC5), Rijndael, RSA (which is an Internet encryption and authentication system that uses an algorithm developed in 1977 by Ron Rivest, Adi Shamir, and Leonard Adleman), Secure Hash Algorithm (SHA), Secure Socket Layer (SSL), Secure Hypertext Transfer Protocol (HTTPS), and/or the like. Employing such encryption security protocols, the AEW may encrypt all incoming and/or outgoing communications and may serve as node within a virtual private network (VPN) with a wider communications network. The cryptographic component facilitates the process of "security authorization" whereby access to a resource is inhibited by a security protocol wherein the cryptographic component effects authorized access to the secured resource. In addition, the cryptographic component may provide unique identifiers of content, e.g., employing and MD5 hash to obtain a unique signature for an digital audio file. A cryptographic component may communicate to and/or with other components in a component collection, including itself, and/or facilities of the like. The cryptographic component supports encryption schemes allowing for the secure transmission of information across a communications network to enable the AEW component to engage in secure transactions if so desired. The cryptographic component facilitates the secure accessing of resources on the AEW and facilitates the access of secured resources on remote systems; i.e., it may act as a client and/or server of secured resources. Most frequently, the cryptographic component communicates with information servers, operating systems, other program components, and/or the like. The cryptographic component may contain, communicate, generate, obtain, and/or provide program component, system, user, and/or data communications, requests, and/or responses.

The AEW Database

The AEW database component 2319 may be embodied in a database and its stored data. The database is a stored program component, which is executed by the CPU; the stored program component portion configuring the CPU to process the stored data. The database may be a conventional, fault tolerant, relational, scalable, secure database such as Oracle or Sybase. Relational databases are an extension of a flat file. Relational databases consist of a series of related tables. The tables are interconnected via a key field. Use of the key field allows the combination of the tables by indexing against the key field; i.e., the key fields act as dimensional pivot points for combining information from various tables. Relationships generally identify links maintained between tables by matching primary keys. Primary keys represent fields that uniquely identify the rows of a table in a relational database. More precisely, they uniquely identify rows of a table on the "one" side of a one-to-many relationship.

Alternatively, the AEW database may be implemented using various standard data-structures, such as an array, hash, (linked) list, struct, structured text file (e.g., XML), table, and/or the like. Such data-structures may be stored in memory and/or in (structured) files. In another alternative, an object-oriented database may be used, such as Frontier, ObjectStore, Poet, Zope, and/or the like. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the AEW database is implemented as a data-structure, the use of the AEW database 2319 may be integrated into another component such as the AEW component 2335. Also, the database may be implemented as a mix of data structures, objects, and relational structures. Databases may be consolidated and/or distributed in countless variations through standard data processing techniques. Portions of databases, e.g., tables, may be exported and/or imported and thus decentralized and/or integrated.

In one embodiment, the database component 2319 includes several tables 2319a-e. A samples table 2319a may include fields such as, but not limited to: user_id, name, contact_info, account_identifier, parent_account_identifier, market participant_id, login, password, private_key, public_key, user_interface_interactions, content_ID, ad_ID, device_ID, sample_id, and/or the like. The user table may support and/or track multiple entity accounts on a AEW. A models table 2319b may include fields such as, but not limited to: model_ID, user_ID, model_type, device_make, device_model, model capabilities, last_synchronization-_time, ad_ID, and/or the like. An estimation parameters table 2319c may include fields such as, but not limited to: S0_id,t10_id, and/or the like. An graphs table 2319d may include fields such as, but not limited to: graphs_mean, graph_ROI, and/or the like. An past_data 2319*d* may include fields such as, but not limited to: past data, past_data_timestamp, and/or the like.

In one embodiment, the AEW database may interact with other database systems. For example, employing a distributed database system, queries and data access by search AEW component may treat the combination of the AEW database, an integrated data security layer database as a single database entity.

In one embodiment, user programs may contain various user interface primitives, which may serve to update the AEW. Also, various accounts may require custom database tables depending upon the environments and the types of clients the AEW may need to serve. It should be noted that any unique fields may be designated as a key field throughout. In an alternative embodiment, these tables have been decentralized into their own databases and their respective database controllers (i.e., individual database controllers for each of the above tables). Employing standard data processing techniques, one may further distribute the databases over several computer systemizations and/or storage devices. Similarly, configurations of the decentralized database controllers may be varied by consolidating and/or distributing the various database components 2319*a-e*. The AEW may be configured to keep track of various settings, inputs, and parameters via database controllers.

The AEW database may communicate to and/or with other components in a component collection, including itself, and/or facilities of the like. Most frequently, the AEW database communicates with the AEW component, other program components, and/or the like. The database may contain, retain, and provide information regarding other nodes and data.

The AEWs

The AEW component 2335 is a stored program component that is executed by a CPU. In one embodiment, the AEW component incorporates any and/or all combinations of the aspects of the AEW that was discussed in the previous figures. As such, the AEW affects accessing, obtaining and the provision of information, services, transactions, and/or the like across various communications networks.

The AEW component enabling access of information between nodes may be developed by employing standard development tools and languages such as, but not limited to: Apache components, Assembly, ActiveX, binary executables, (ANSI) (Objective-) C (++), C# and/or .NET, database adapters, CGI scripts, Java, JavaScript, mapping tools, procedural and object oriented development tools, PERL, PHP, Python, shell scripts, SQL commands, web application server extensions, web development environments and libraries (e.g., Microsoft's ActiveX; Adobe AIR, FLEX & FLASH; AJAX; (D)HTML; Dojo, Java; JavaScript; jQuery(UI); MooTools; Prototype; script.aculo.us; Simple Object Access Protocol (SOAP); SWFObject; Yahoo! User Interface; and/or the like), WebObjects, and/or the like. In one embodiment, the AEW server employs a cryptographic server to encrypt and decrypt communications. The AEW component may communicate to and/or with other components in a component collection, including itself, and/or facilities of the like. Most frequently, the AEW component communicates with the AEW database, operating systems, other program components, and/or the like. The AEW may contain, communicate, generate, obtain, and/or provide program component, system, user, and/or data communications, requests, and/or responses.

Distributed AEWs

The structure and/or operation of any of the AEW node controller components may be combined, consolidated, and/or distributed in any number of ways to facilitate development and/or deployment. Similarly, the component collection may be combined in any number of ways to facilitate deployment and/or development. To accomplish this, one may integrate the components into a common code base or in a facility that can dynamically load the components on demand in an integrated fashion.

The component collection may be consolidated and/or distributed in countless variations through standard data processing and/or development techniques. Multiple instances of any one of the program components in the program component collection may be instantiated on a single node, and/or across numerous nodes to improve performance through load-balancing and/or data-processing techniques. Furthermore, single instances may also be distributed across multiple controllers and/or storage devices; e.g., databases. All program component instances and controllers working in concert may do so through standard data processing communication techniques.

The configuration of the AEW controller will depend on the context of system deployment. Factors such as, but not limited to, the budget, capacity, location, and/or use of the underlying hardware resources may affect deployment requirements and configuration. Regardless of if the configuration results in more consolidated and/or integrated program components, results in a more distributed series of program components, and/or results in some combination between a consolidated and distributed configuration, data may be communicated, obtained, and/or provided. Instances of components consolidated into a common code base from the program component collection may communicate, obtain, and/or provide data. This may be accomplished through intra-application data processing communication techniques such as, but not limited to: data referencing (e.g., pointers), internal messaging, object instance variable communication, shared memory space, variable passing, and/or the like.

If component collection components are discrete, separate, and/or external to one another, then communicating, obtaining, and/or providing data with and/or to other component components may be accomplished through inter-application data processing communication techniques such as, but not limited to: Application Program Interfaces (API) information passage; (distributed) Component Object Model ((D)COM), (Distributed) Object Linking and Embedding ((D)OLE), and/or the like), Common Object Request Broker Architecture (CORBA), local and remote application program interfaces Jini, Remote Method Invocation (RMI), SOAP, process pipes, shared files, and/or the like. Messages sent between discrete component components for inter-application communication or within memory spaces of a singular component for intra-application communication may be facilitated through the creation and parsing of a grammar. A grammar may be developed by using standard development tools such as lex, yacc, XML, and/or the like, which allow for grammar generation and parsing functionality, which in turn may form the basis of communication messages within and between components. For example, a grammar may be arranged to recognize the tokens of an HTTP post command, e.g.:

w3c-post http:// . . . Value1 where Value1 is discerned as being a parameter because "http://" is part of the grammar syntax, and what follows is considered part of the post value. Similarly, with such a grammar, a variable "Value1" may be inserted into an "http://" post command and then sent. The grammar syntax itself may be presented as structured data that is interpreted and/or otherwise used to generate the parsing mechanism (e.g., a syntax description text file as processed by lex, yacc, etc.). Also, once the parsing mechanism is generated and/or instantiated, it itself may process and/or parse structured data such as, but not limited to: character (e.g., tab) delineated text, HTML, structured text streams, XML, and/or the like structured data. In another embodiment, inter-application data processing protocols themselves may have integrated and/or readily available parsers (e.g., the SOAP parser) that may be employed to parse (e.g., communications) data. Further, the parsing grammar may be used beyond message parsing, but may also be used to parse: databases, data collections, data stores, structured data, and/or the like. Again, the desired configuration will depend upon the context, environment, and requirements of system deployment.

In order to address various issues and improve over previous works, the application is directed to APPARATUSES, METHODS AND SYSTEMS FOR ESTIMATING WATER DIFFUSIVITY AND MICROCIRCULATION OF BLOOD USING DW-MRI DATA. The entirety of this application (including the Cover Page, Title, Headings, Field, Background, Summary, Brief Description of the Drawings, Detailed Description, Claims, Abstract, Figures, and otherwise) shows by way of illustration various embodiments in which the claimed inventions may be practiced. The advantages and features of the application are of a representative sample of embodiments only, and are not exhaustive and/or exclusive. They are presented only to assist in understanding and teach the claimed principles. It should be understood that they are not representative of all claimed inventions. As such, certain aspects of the subject matter have not been discussed herein. That alternate embodiments may not have been presented for a specific portion of the invention or that further undescribed alternate embodiments may be available for a portion is not to be considered a disclaimer of those alternate embodiments. It will be appreciated that many of those undescribed embodiments incorporate the same principles of the invention and others are equivalent. Thus, it is to be understood that other embodiments may be utilized and functional, logical, organizational, structural and/or topological modifications may be made without departing from the scope and/or spirit of the subject matter. As such, all examples and/or embodiments are deemed to be non-limiting throughout this subject matter. Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the subject matter. Furthermore, it is to be understood that such features are not limited to serial execution, but rather, any number of threads, processes, services, servers, and/or the like that may execute asynchronously, concurrently, in parallel, simultaneously, synchronously, and/or the like are contemplated by the subject matter. As such, some of these features may be mutually contradictory, in that they cannot be simultaneously present in a single embodiment. Similarly, some features are applicable to one aspect of the invention, and inapplicable to others. In addition, the subject matter includes other inventions not presently claimed. Applicant reserves all rights in those presently unclaimed inventions including the right to claim such inventions, file additional applications, continuations, continuations in part, divisions, and/or the like thereof. As such, it should be understood that advantages, embodiments, examples, functional, features, logical, organizational, structural, topological, and/or other aspects of the subject matter are not to be considered limitations on the subject matter as defined by the claims or limitations on equivalents to the claims. It is to be understood that, depending on the particular needs and/or characteristics of a AEW individual and/or enterprise user, database configuration and/or relational model, data type, data transmission and/or network framework, mathematical equation, and/or the like, various embodiments of the AEW, may be implemented that enable a great deal of flexibility and customization. While various embodiments and discussions of the AEW have been directed to malignant tissues, however, it is to be understood that the embodiments described herein may be readily configured and/or customized for a wide variety of other applications and/or implementations.

What is claimed is:

1. A computer processor implemented method for outputting an optimally modelled coefficient for a voxel in diffusion weighted magnetic resonance imaging, the method comprising:
  (a) applying, using a processor, a mono-exponential model to signal intensities for a set of b-values at a particular voxel in a region of interest (ROI) received from an imaging device;
  (b) estimating, using a processor, a goodness of fit of the model applied in (a) by comparing the model to the signal intensities for b-values below a predetermined b-value at the particular voxel, wherein the estimating includes:
    (b1) determining, using a processor, an R-square coefficient ($R^2$) between the mono-exponential model and the signal intensities for the set of b-values at the particular voxel according to the formula $$R^2 = 1 - SS_{res}/SS_{tot}$$

where $SS_{res}$ is a residual sum of squares and $SS_{tot}$ is a total sum of squares;
    (b2) determining, using a processor, an adjusted $R^2$ coefficient according to the formula $$\text{adjusted } R^2 = 1 - (1-R^2)*(n-1)/n-p-1$$

where n is the number of b-values used and p is the number of parameters used from the mono-exponential model; and
    (b3) outputting the adjusted-$R^2$ coefficient as a measure of the goodness of fit;
  (c) if the goodness of fit is less than a predetermined goodness threshold at the particular voxel, applying, using a processor, an intravoxel-incoherent-motion (IVIM) model to the signal intensities for the set of b-values at the particular voxel and determining a perfusion fraction parameter (f), true-diffusion coefficient (D) and micro-perfusion coefficient (D*) using the IVIM model;

(d) outputting an apparent diffusion coefficient (ADC) determined from the mono-exponential model for the particular voxel, if (i) the goodness of fit is not less than the predetermined goodness threshold, (ii) f is equal to a lower bound of a predetermined fraction range used in applying the IVIM model in (c), or (iii) D*/D is less than 10; and (e) outputting the true diffusion (D) determined from the IVIM model for the particular voxel, if (i) the goodness of fit is less than the predetermined goodness threshold, (ii) f is not equal to the lower bound of the predetermined fraction range used in applying the IVIM model in (c), and (iii) D*/D is not less than 10.

2. The computer processor implemented method of claim 1, wherein step (b) comprises determining, using a processor, a root-mean-square error (RMSE) between the mono-exponential model and the signal intensities for the set of b-values at the particular voxel and outputting the RMSE as a measure of the goodness of fit.

3. The computer processor implemented method of claim 1, further comprising repeating steps (a) through (e) for a plurality of voxels in the ROI.

4. The computer processor implemented method of claim 3, further comprising generating, using a processor, a map for each voxel in the ROI indicating whether the ADC or the true diffusion was output at steps (d) and (e), respectively.

5. The computer processor implemented method of claim 1, wherein the predetermined b-value is 300 s/mm$^2$.

6. The computer processor implemented method of claim 1, wherein the set of b-values includes five or fewer b-values.

7. A computer processor implemented method for modeling a portion of a diffusion weighted magnetic resonance image, the method comprising:

(a) determining, using a processor, a perfusion fraction parameter (f), micro-perfusion coefficient (D*) and adjusted slope (a) using a non-linear least-squares fitting technique to fit the formula $$S_{low\_b}S_0*(-a*b+(1-f)+f*\exp(-b*D*))$$

to signal intensities at a particular voxel in a region of interest (ROI) received from an imaging device for at least three b-values below a predetermined b-value threshold;

(b) using f, D* and a determined in step (a) to determine, using a processor, a true-diffusion coefficient (D); and (c) determining, using a processor, a signal attenuation $S_b$ for a b-value greater than the predetermined b-value threshold using D determined in step (b) and the formula $$S_b = S_{0\_\text{diffusion}} * \exp(-b*D)$$

where $S_{0\_\text{diffusion}}$ is the signal intensity of true-diffusion at b=0.

8. The computer processor implemented method of claim 7, further comprising:

(d) using D determined in step (b) to determine, using a processor, a kurtosis coefficient $K_{app}$ from the formula:

$$S_b = S_0 * \exp(-b*D + 1/6*b^2*D^2*K_{app})$$

9. The computer processor implemented method of claim 8, further comprising repeating steps (a) through (d) for a plurality of voxels in the ROI.

10. The computer processor implemented method of claim 9, further comprising:

(e) comparing, using a processor, $K_{app}$ determined in step (d) for each voxel to low kurtosis threshold and a high kurtosis threshold; and (f) generating, using a processor, a classification map for each voxel in the ROI indicating whether $K_{app}=0$, whether $K_{app}$ is less than the low kurtosis threshold or whether $K_{app}$ is greater than the high kurtosis threshold.

11. The computer processor implemented method of claim 7, wherein the predetermined b-value is 300 s/mm$^2$.

12. The computer processor implemented method of claim 7, wherein the at least three b-values includes five or fewer b-values.

* * * * *